(12) United States Patent
Zhang et al.

(10) Patent No.: US 11,737,877 B2
(45) Date of Patent: Aug. 29, 2023

(54) ADJUSTABLE HEART VALVE REPAIR SYSTEM

(71) Applicant: Hangzhou Valgen Medtech Co., Ltd., Hangzhou (CN)

(72) Inventors: Tingchao Zhang, Hangzhou (CN); Weiwei Zhang, Hangzhou (CN); Xianzhang Zheng, Hangzhou (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 511 days.

(21) Appl. No.: 16/976,343

(22) PCT Filed: May 22, 2019

(86) PCT No.: PCT/CN2019/087886
§ 371 (c)(1),
(2) Date: Aug. 27, 2020

(87) PCT Pub. No.: WO2019/233279
PCT Pub. Date: Dec. 12, 2019

(65) Prior Publication Data
US 2021/0038387 A1    Feb. 11, 2021

(30) Foreign Application Priority Data

Jun. 8, 2018 (CN) .......... 201810588221.3
Jun. 8, 2018 (CN) .......... 201820892815.9

(51) Int. Cl.
*A61F 2/24* (2006.01)
*A61B 17/04* (2006.01)
*A61B 17/34* (2006.01)

(52) U.S. Cl.
CPC ........ *A61F 2/2466* (2013.01); *A61B 17/0469* (2013.01); *A61B 17/3468* (2013.01); *A61F 2220/0075* (2013.01)

(58) Field of Classification Search
CPC ........... A61F 2/2466; A61F 2220/0075; A61B 17/0469; A61B 17/3468; A61B 17/0487;
(Continued)

(56) References Cited

U.S. PATENT DOCUMENTS 7,335,213 B1    2/2008 Hyde et al.
2003/0204205 A1    10/2003 Sauer et al.
(Continued)

FOREIGN PATENT DOCUMENTS

CN    103251464 A    8/2013
CN    103826570 A    5/2014
(Continued)

OTHER PUBLICATIONS

The International Search Report issued corresponding PCT application No. PCT/CN2019/087886 dated Jul. 29, 2019.
(Continued)

*Primary Examiner* — Timothy J Neal
*Assistant Examiner* — Mohammed S Adam
(74) *Attorney, Agent, or Firm* — Hauptman Ham, LLP

(57) ABSTRACT

An adjustable heart valve repair system includes a suture implanting apparatus and a suture locker. The suture implanting apparatus is operable to implant a suture into at least one leaflet of a heart valve. The suture locker is operable to fix the suture. The suture locker includes an adjusting device to adjust tensioning or loosening of the suture.

20 Claims, 41 Drawing Sheets

(58) Field of Classification Search
CPC .... A61B 2017/0488; A61B 2017/0409; A61B 2017/0495; A61B 2017/0496
See application file for complete search history.

(56) References Cited

U.S. PATENT DOCUMENTS

| | | |
|---|---|---|
| 2010/0094314 A1 | 4/2010 | Hernlund et al. |
| 2013/0110230 A1 | 5/2013 | Solem |
| 2015/0135057 A1 | 5/2015 | Metcalf et al. |
| 2016/0317144 A1* | 11/2016 | Popovici ............ A61B 17/0469 |
| 2018/0103947 A1* | 4/2018 | Nobles ............... A61B 17/0483 |

FOREIGN PATENT DOCUMENTS

| | | |
|---|---|---|
| CN | 104248457 A | 12/2014 |
| CN | 104367351 A | 2/2015 |
| CN | 104665888 A | 6/2015 |
| CN | 104939949 A | 9/2015 |
| CN | 105246431 A | 1/2016 |
| CN | 107468378 A | 12/2017 |
| CN | 107569301 A | 1/2018 |
| CN | 108186163 A | 6/2018 |
| CN | 109199468 A | 1/2019 |
| EP | 3157607 A2 | 4/2017 |
| WO | 2017066888 A1 | 4/2017 |

OTHER PUBLICATIONS

The International Search Report issued corresponding PCT application No. PCT/CN2018/096901 dated Sep. 26, 2018.
The Extended European Search Report issued corresponding EP Application No. EP 19816090.5, dated Jun. 8, 2021.

* cited by examiner

ADJUSTABLE HEART VALVE REPAIR SYSTEM

RELATED APPLICATIONS

The present application is a National Phase of International Application Number PCT/CN2019/087886, filed on May 22, 2019, which claims priority to Chinese Patent Application No. 201810588221.3, filed on Jun. 8, 2018, and Chinese Patent Application No. 201820892815.9, filed on Jun. 8, 2018.

TECHNICAL FIELD

This disclosure belongs to the field of medical appliances, and relates to an adjustable heart valve repair system.

BACKGROUND

A mitral valve is a one-way "valve" between a left atrium and a left ventricle and can ensure blood flow from the left atrium to the left ventricle. The mitral valve includes two leaflets, i.e., an anterior leaflet and a posterior leaflet. When the left ventricle is in a diastolic state, the anterior leaflet and the posterior leaflet are apart from each other, and the blood flows from the left atrium to the left ventricle. When the left ventricle is in a contracted state, chordae tendineae are stretched to prevent the leaflets from being washed by the blood flow to the left atrium. FIG. 1A and FIG. 1B illustrate a mitral valve in a health state, where the anterior leaflet and the posterior leaflet are in a good close state to ensure blood flow from the left ventricle to an aorta through an aortic valve (AV). A mitral valve illustrated in FIG. 2A and FIG. 2B has lesions. Different from the mitral valve in the health state, under the condition that the mitral valve has lesions, the mitral valve cannot return to a close state when the left ventricle is in the contracted state, and the momentum of the blood flow can further cause the leaflet to fall into the left atrium, thereby resulting in blood regurgitation, called "mitral regurgitation".

At present, surgical methods such as surgical suture implantation or edge-to-edge repair for the leaflet are used to treat the mitral regurgitation. All these surgeries require invasive thoracotomy, with general anesthesia and moderate hypothermic cardiopulmonary bypass (MHCB) as auxiliary supports, thereby resulting in defects such as complicated surgical procedure, high surgical cost, high patient trauma, high risk of complications, long hospital stay, painful recovery process and the like.

SUMMARY

Aiming at the above-mentioned defects in the related art, the technical problem to be solved by the present disclosure is to provide an adjustable heart valve repair system. One or more sutures are implanted into an anterior leaflet or a posterior leaflet of a mitral valve to be taken as "artificial chordae tendineae", thereby achieving "chordae tendineae repair" to treat the mitral regurgitation. Alternatively, multiple sutures are first and respectively implanted into the anterior leaflet and the posterior leaflet of the mitral valve. The multiple sutures are then fixed together to pull the anterior leaflet and the posterior leaflet toward each other, thereby reducing or eliminating a gap between the anterior leaflet and the posterior leaflet of the mitral valve to achieve "edge-to-edge repair". The adjustable heart valve repair system provided in the present disclosure is particularly suitable for transapical minimally invasive repair surgery, which has advantages such as simple surgical procedure, low operation cost, low patient trauma, low risk of complications, and rapid recovery process. In addition, before fixing the suture by an operator, tightness of the suture can be adjusted to adjust the gap between the anterior leaflet and the posterior leaflet of the mitral valve. Meanwhile, the mitral regurgitation is monitored via a medical imaging device to ensure that no mitral regurgitation occurs or the mitral regurgitation is slightest.

The technical solution adopted by the present disclosure to solve the technical problem is as follows.

An adjustable heart valve repair system includes a suture implanting apparatus and a suture locker. The suture implanting apparatus is operable to implant a suture into at least one leaflet of a heart valve. The suture locker is operable to fix the suture and includes a lock pin, an outer shaft, a handle, and an adjusting device. The lock pin is operable to receive or fix the suture. The outer shaft defines a receiving cavity, and the lock pin is disposed at a distal end of the receiving cavity. The handle includes a fixing portion, where the fixing portion is coupled to a proximal end of the outer shaft. The adjusting device is disposed on the fixing portion, where the adjusting device is coupled to a proximal end of the suture and operable to adjust tensioning or loosening of the suture.

The adjustable heart valve repair system according to the present disclosure is especially suitable for transapical valve repair surgery for treating the mitral regurgitation and can quickly realize chordae tendineae repair or edge-to-edge repair for the leaflet of the mitral valve. When in use, only a small incision ranging from 1 cm to 5 cm in diameter is formed in patient's chest, the apex of the heart is punctured, and sutures are implanted into the leaflet. The distal ends of the sutures are then fixed to a ventricle wall or papillary muscle to act as artificial chordae tendinea to realize the "chordae tendinea repair". Alternatively, the suture locker is used to fix multiple sutures in the leaflet together, thereby pulling the anterior leaflet and the posterior leaflet of the mitral valve toward each other to reduce or eliminate the gap between the leaflets, so that the mitral valve repaired has a double-orifice structure to achieve "edge-to-edge repair". Therefore, the adjustable heart valve repair system according to the present disclosure can treat degenerative mitral regurgitation and functional mitral regurgitation. The entire surgical procedure only forms a relatively small wound in the patient's chest, which is minimally invasive and avoids damages to the patient done by a traditional thoracotomy surgery. The instrument is easy to operate, thereby avoiding cumbersome steps of transcatheter mitral valve repair in the related art and resulting in a high surgical success rate and relatively short operation time.

In addition, the operator can adjust the gap between the anterior leaflet and the posterior leaflet of the mitral valve before using the suture locker to hold and fix the suture. Meanwhile, the mitral regurgitation is observed through a medical imaging device. When the mitral regurgitation becomes slightest or completely eliminated, the lock pin is held and pressed to fix the suture, so as to ensure the surgical effect and improve the surgical success rate.

BRIEF DESCRIPTION OF THE ACCOMPANYING DRAWINGS

To illustrate the technical solution in the implementations of the present disclosure more clearly, the following briefly introduces the accompanying drawings required for describing the implementations. Obviously, the accompanying drawings in the following description are merely some implementations of the present disclosure, and based on these accompanying drawings, those of ordinary skill in the art may also derive other accompanying drawings without creative efforts.

FIG. 27B is a cross-sectional view of the handle illustrated in FIG. 27A, taken along line D-D.

FIG. 35A is an enlarged view of a portion C of FIG. 34B.

DETAILED DESCRIPTION OF ILLUSTRATED IMPLEMENTATIONS

The technical solution in the implementations of the present disclosure will be described clearly and completely hereinafter with reference to the accompanying drawings in the implementations of the present disclosure. Obviously, the described implementations are merely some but not all implementations of the present disclosure. Based on the implementations of the present disclosure, all other implementations obtained by a person of ordinary skill in the art without creative efforts shall fall within the protection scope of the present disclosure.

Orientation definition: an orientation close to an operator is defined as a proximal end, and another orientation away from the operator is defined as a distal end.

Figures 1A, 1B:
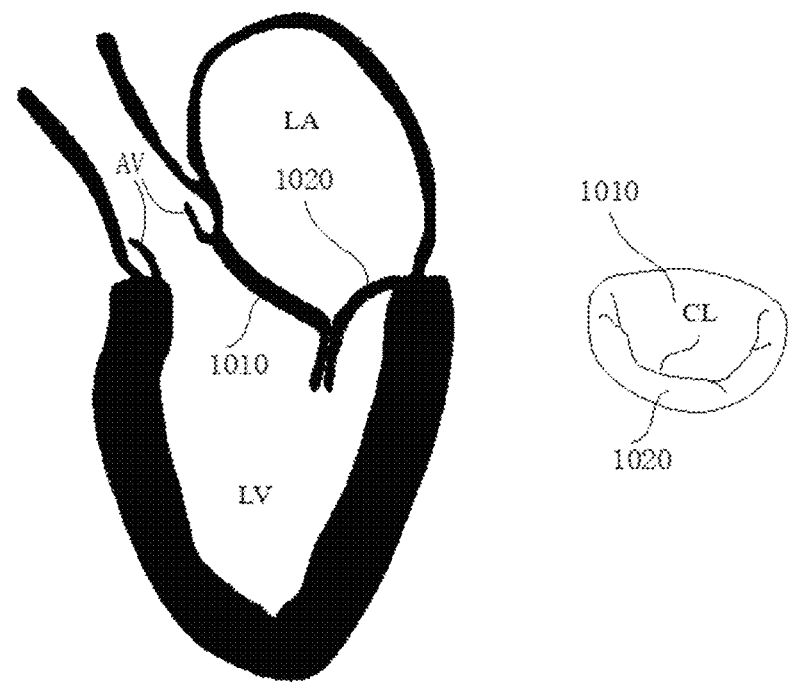
FIGS. 1A-1B are schematic views illustrating a mitral valve in a normal close state in a heart.
Figures 2A, 2B:
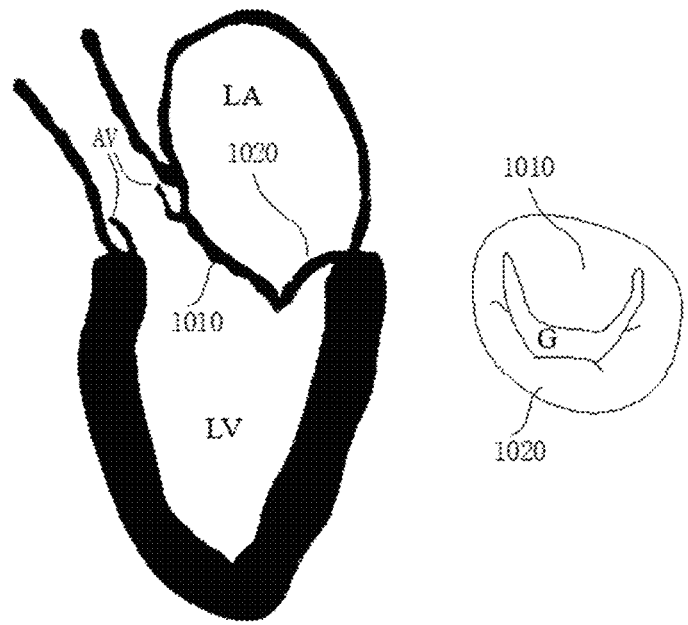
FIGS. 2A-2B are schematic views illustrating a mitral valve in an abnormal close state in a heart.
Figure 3:
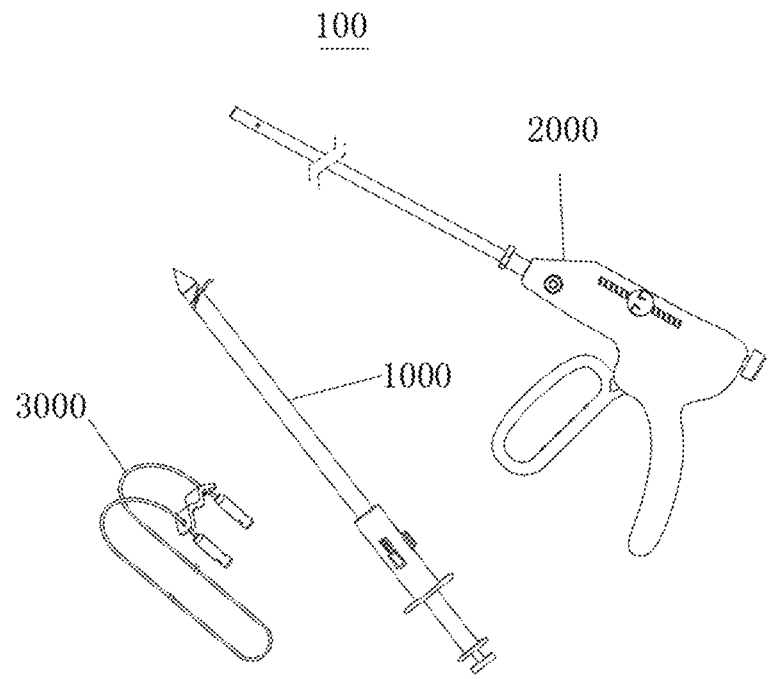
FIG. 3 is a schematic structural view illustrating an adjustable heart valve repair system according to the present disclosure.

As illustrated in FIG. 3, an adjustable heart valve repair system 100 according to the present disclosure includes a suture implanting apparatus 1000 and a suture locker 2000. The suture implanting apparatus 1000 is operable to implant at least one suture 3000 into at least one leaflet of a heart valve. The suture locker 2000 is operable to fix the suture 3000.

Figure 7:
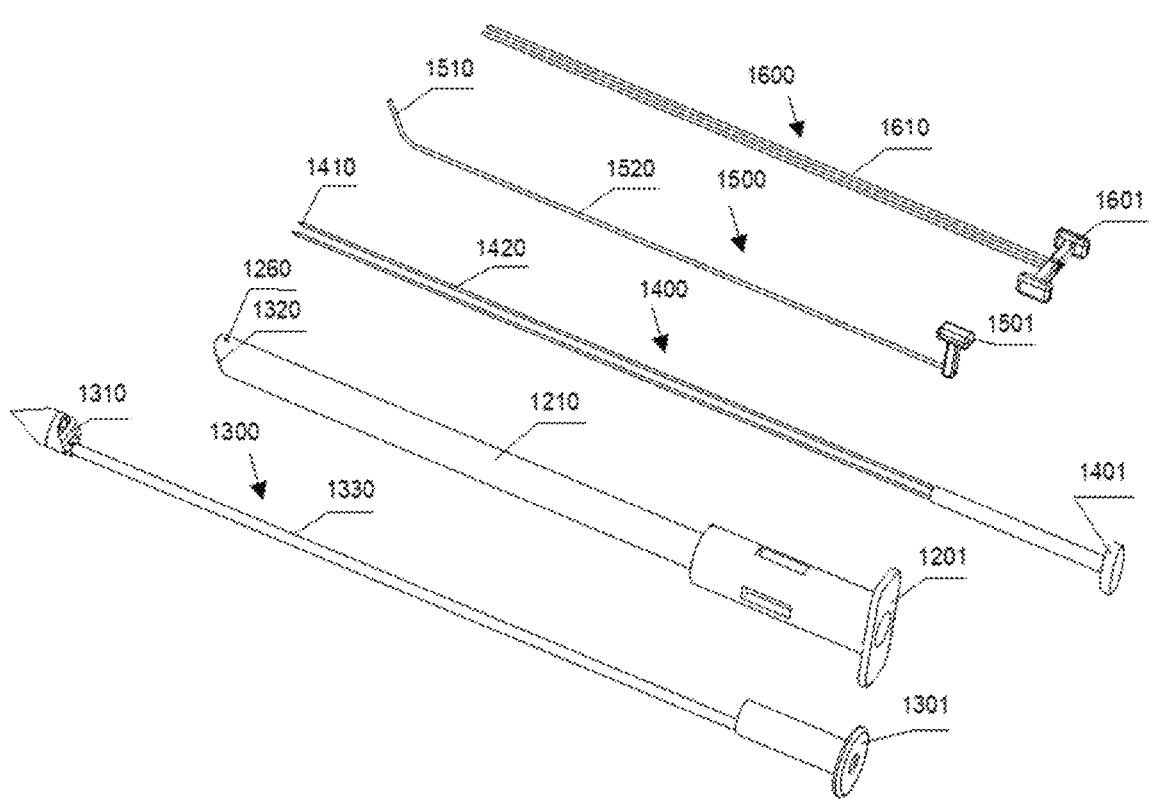
FIG. 7 is an exploded perspective view of the suture implanting apparatus illustrated FIG. 6.

As illustrated in FIG. 7, suture implanting apparatus 1000 includes a pushing shaft 1210, a clamping assembly 1300 for clamping the leaflet, and a puncturing assembly 1400 for puncturing the leaflet. The clamping assembly 1300 and the puncturing assembly 1400 are movably received in the pushing shaft 1210. The suture 3000 is received in the clamping assembly 1300. For ease of use, the suture 3000 may be installed in the suture implanting apparatus 1000 in the factory. It is to be understood that for the convenience of implanting multiple sutures 3000 during a surgery, the suture 3000 may be installed in the suture implanting apparatus 1000 by the operator before or during the surgery.

Figure 4:
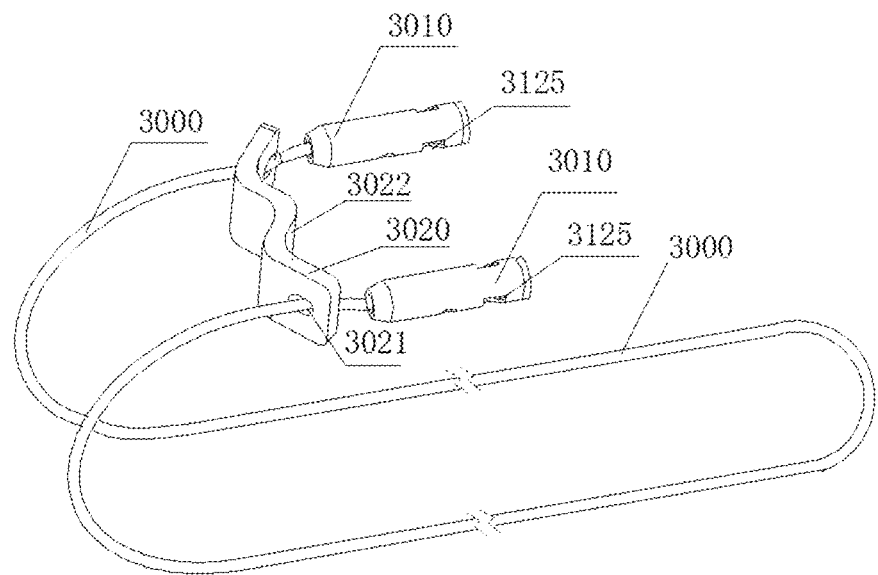
FIG. 4 is a schematic structural view illustrating a suture illustrated in FIG. 3.

As illustrated in FIG. 4 and FIGS. 5A-5C, the suture 3000 has a certain axial length and is flexible. At least one of two ends of the suture 3000 is coupled to a fixing member 3010. The fixing member 3010 is coupled to the puncturing assembly 1400 in a non-detachable fixing manner or a detachable fixing manner. In this implementation, each end of the suture 3000 is preferably coupled with one fixing member 3010 (as illustrated in FIG. 4).

When used for chordae tendineae repair, each suture 3000 is partially fixed to the leaflet, and the two ends of each suture 3000 are fixed to a ventricular wall, an apex of the heart, or a papillary muscle by the suture locker 2000, such that instead of the diseased natural chordae tendineae, the suture 3000 is used to pull the anterior leaflet or the posterior leaflet of the mitral valve. When used for edge-to-edge repair, multiple sutures 3000 are used, each suture 3000 is partially fixed to the leaflet, and all the sutures 3000 are fixed together by the suture locker 2000 to pull the leaflets toward each other. The suture 3000 being flexible refers to that the suture 3000 can be bent arbitrarily without being axially stretched. The suture 3000 may be made from a biocompatible polymer material or a relatively soft metal material, and may be preferably made from a polymer material such as Polytetrafluoroethylene (PTFE) or polypropylene (PP). In this implementation, ePTFE is used.

Figure 5A:
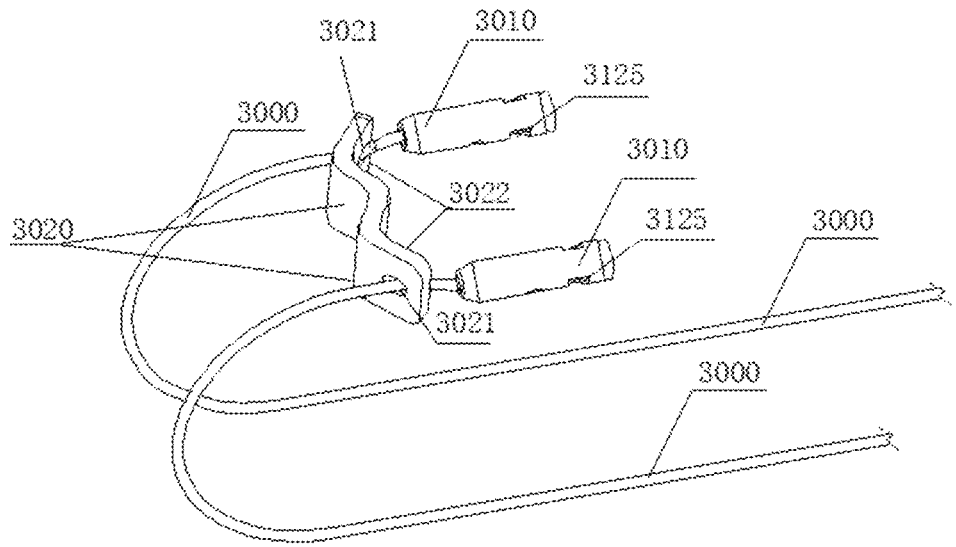
FIGS. 5A-5C are schematic structural views illustrating sutures according to different implementations.
Figure 5B:
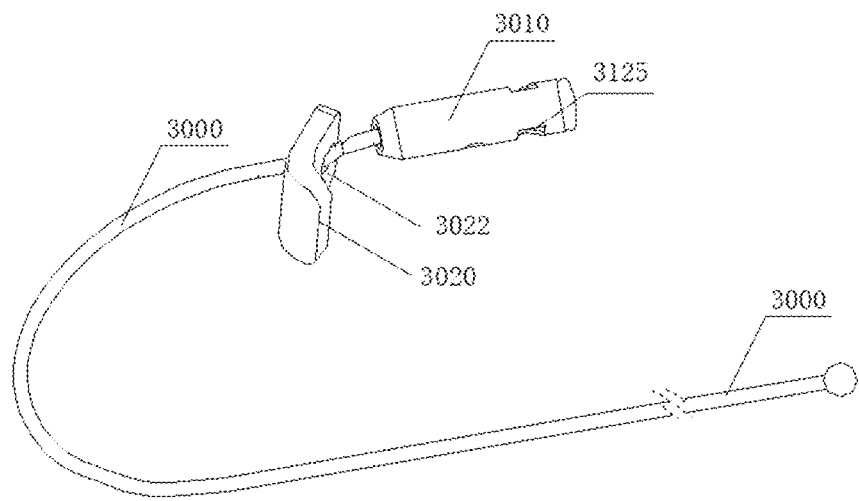
Figure 5C:
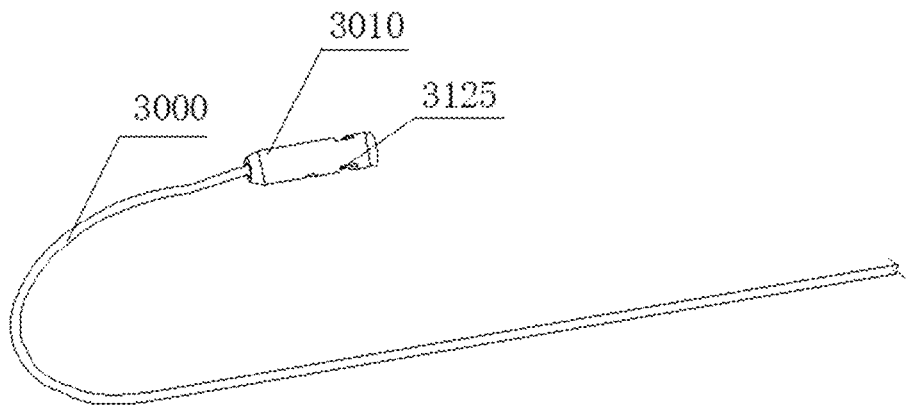

As illustrated in FIG. 4, two fixing members 3010 may be coupled with the two ends of the suture 3000, respectively. Alternatively, as illustrated in FIGS. 5A-5C, only one end of the suture 3000 is coupled with one fixing member 3010. Each time the operator operates the suture implanting apparatus 1000, one or more sutures 3000 can be implanted. The suture 3000 is fixed to the fixing member 3010 in a fixing manner which includes but is not limited to knotting, winding, welding, bonding, snapping, or the like. For example, after one end of the suture 3000 passes through the fixing member 3010, the end of the suture 3000 is knotted to form a coil with a relatively large diameter. For another example, the distal end of the suture 3000 is welded to form a ball with a relatively large diameter. For yet another example, the suture 3000 is provided with a lateral positioning rod at the distal end thereof. When only one end of the suture 3000 is coupled with one fixing member 3010, since the other end of the suture 3000 is not coupled with one fixing member 3010, as illustrated in FIG. 5B, the diameter of the other end needs to be set to be larger than the diameter of the suture 3000 by knotting, winding, setting a spherical end, setting a disc-shaped end, or the like. In such a case that the suture 3000 is implanted into the leaflet, after one end of the suture 3000 is coupled with the puncturing assembly 1400 via the fixing member 3010, the suture 3000 is drawn back, and the other end of the suture 3000 with a relatively large diameter is fixed to an upper surface of the leaflet.

The fixing member 3010 is coupled with the puncturing assembly 1400 in a detachable fixed connection manner or a non-detachable fixed connection manner. The connection manner used is adapted to the shape of the fixing member 3010. The fixing member 3010 is generally in the shape of a cylinder, and the cross section of the fixing member 3010 may be in the shape of a circle, an ellipse, a polygon, or the like, and preferably in the shape of a circle or an ellipse.

In order to change a contact between the suture 3000 and the leaflet from a point contact to a surface contact to reduce a risk that the suture 3000 tears up the leaflet, the suture 3000 is preferably sleeved with an anti-slip member 3020. The anti-slip member 3020 can slide along an axial direction of the suture 3000. Since the anti-slip member 3020 is sleeved on the suture 3000 in advance, after a puncturing needle 1410 of the suture implanting apparatus 1000 punctures the leaflet and is coupled with the fixing member 3010 positioned at the distal end of the suture 3000, the anti-slip member 3020 can be driven to a puncturing point and is fixed to the leaflet together with the suture 3000. The anti-slip member 3020 defines at least one through hole 3021. The suture 3000 passes through the through hole 3021. The number of the at least one through hole 3021 is related to the manner in which the anti-slip member 3020 is fixed. In an implementation, the anti-slip member 3020 defines at least two through holes 3021, and the two ends of the suture 3000 respectively pass through the through holes 3021 and are then respectively coupled to two fixing members 3010 (as illustrated in FIG. 4). In another implementation, the anti-slip member 3020 defines one through hole 3021, and one end of the suture 3000 passes through the through hole 3021 and is then coupled to the fixing member 3010 (as illustrated in FIGS. 5A-5B). In order to prevent the anti-slip member 3020 from slipping off the suture 3000, the diameter of the through hole 3021 is smaller than the diameter of the fixing member 3010, and the other end of the suture 3000 at which the fixing member 3010 is absent needs to be set to have a diameter larger than that the diameter of the through hole 3021 defined in the anti-slip member 3020 through knotting, setting the spherical end, setting the disc-shaped end, or the like (as illustrated in FIG. 5B).

In order to disperse a force applied against the leaflet by the suture 3000 to a contact surface between the anti-slip member 3020 and the leaflet to the greatest extent, the anti-slip member 3020 needs to be as close as possible to the leaflet, and thus the anti-slip member 3020 has an abutted surface 3022 that abuts against the leaflet. Except for the abutted surface 3022, there is no limitation on the specific structure of the anti-slip member 3020. For example, the anti-slip member 3020 may be in the shape of a sheet, a disc or a sphere with a certain area, or may even have an irregular shape, and preferably, the anti-slip member 3020 is in the shape of a sheet. The anti-slip member 3020 may have a non-porous structure, a mesh structure, a stripe structure, or the like. The anti-slip member 3020 needs to be made from a biocompatible material, for example, an elastic material or a non-elastic material. Specifically, the anti-slip member 3020 is selected from at least one of an elastic pledget, a patch, a felt sheet, a mesh structure, a disc-shaped structure, or a double-disc structure. The anti-slip member 3020 having the disc-shaped structure or the double-disc structure is similar to an occluder in the related art, and details of the anti-slip member 3020 is not be described in detail herein. Preferably, in order to reduce an overall size of the instrument, the anti-slip member 3020 having the disc-shaped structure or the double-disc structure needs to be made from a shape memory material. In this implementation, a polyester pledget is used as the anti-slip member 3020.

Figure 6:
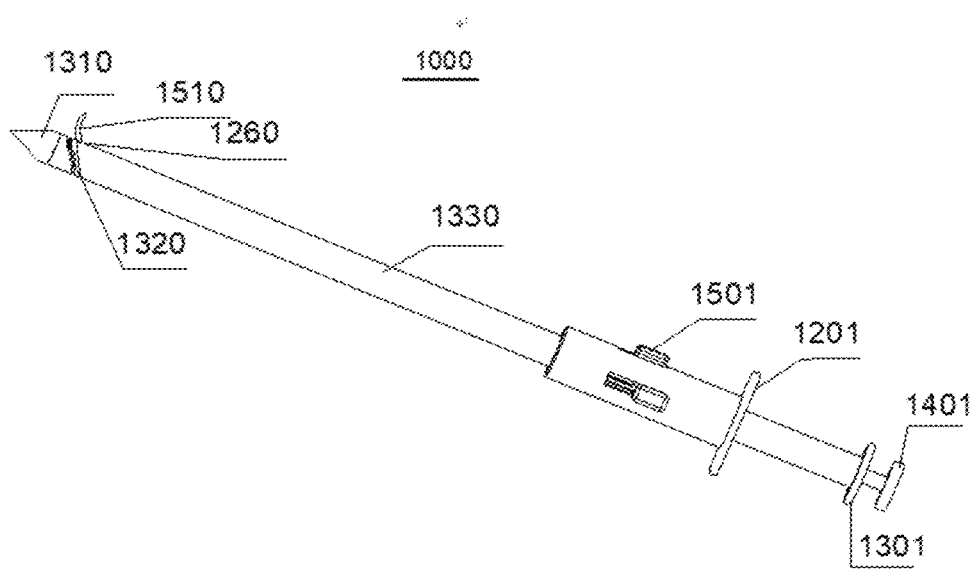
FIG. 6 is a schematic structural view illustrating a suture implanting apparatus illustrated in FIG. 3.
Figure 8:
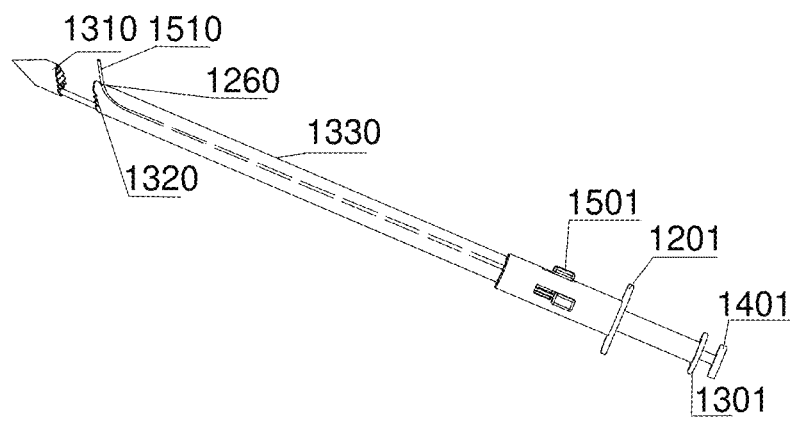
FIG. 8 is a schematic structural view illustrating a clamping assembly of the suture implanting apparatus illustrated in FIG. 6.

The suture implanting apparatus 1000 is used for implanting at least one suture 3000 into the leaflet. As illustrated in FIGS. 6-8, the suture implanting apparatus 1000 includes the clamping assembly 1300, the puncturing assembly 1400 and the pushing shaft 1210. The pushing shaft 1210 has a tubular body with a certain axial length or a rod-shaped body defining a lumen. The pushing shaft 1210 may be a multiple-lumen tube integrally formed. Alternatively, the pushing shaft 1210 may be formed by an outer tube and an inner tube received and fixed in the outer tube. The pushing shaft 1210 may be made from a biocompatible polymer material such as polyformaldehyde (POM), polyethylene (PE), nylon polyamide (PA), polyvinyl chloride (PVC), acrylonitrile butadiene styrene copolymers (ABS), thermoplastic elastomer Pebax or polyurethane (PU), a metal material such as stainless steel or nickel-titanium alloy, or a metal-polymer composite material. In this implementation, the pushing shaft 1210 is a rod-shaped body with multiple lumens that are defined along an axial direction of the pushing shaft 1210 and spaced apart from each other. The pushing shaft 1210 is provided with a first handle 1201 at a proximal end of the pushing shaft 1210. The first handle 1201 is operated to push the pushing shaft 1210 toward the distal end or draw back the pushing shaft 1210 toward the proximal end.

Referring back to FIG. 7, the puncturing assembly 1400 is movably received in one lumen of the pushing shaft 1210. The puncturing assembly 1400 includes at least one puncturing push rod 1420 and at least one puncturing needle 1410 each provided at a distal end of one puncturing push rod 1420. The number of the at least one puncturing push rod 1420 is related to the number of the at least one fixing member 3010. In this implementation, as illustrated in FIG. 4, the suture 3000 is provided with two fixing members 3010 respectively at two ends of the suture 3000, and thus two puncturing push rods 1420 are received in parallel in the pushing shaft 1210, and each puncturing needle 1410 corresponds to one fixing member 3010. After the puncturing needle 1410 punctures the leaflet, the puncturing needle 1410 can be coupled with the fixing member 3010 of the suture 3000. Then, the puncturing push rod 1420 is drawn back to pull the suture 3000 toward the proximal end. A distal end of the puncturing needle 1410 is a straight top end having a tapered shape to facilitate puncturing the leaflet and reducing a diameter of a puncturing point formed on the leaflet. In the related art, a needle having a hooked end is employed to puncture the leaflet, and the needle hooks the suture 3000 and then is drawn back to drive the suture 3000 to pass through the leaflet. A puncturing point on the leaflet formed by the needle having the hooked end has a relatively large diameter, thereby bringing significant damage to the leaflet, and accordingly not only patient's postoperative recovery is affected, but also a risk of tearing of the leaflet after operation is increased. However, the puncturing point on the leaflet formed by the straight distal end having the tapered shape is small, thereby facilitating patient's postoperative recovery. In this implementation, a single puncturing point formed on each leaflet by the suture implanting apparatus 1000 has a diameter falling within a range from 0.3 mm to 1.5 mm. Furthermore, by selecting the puncturing needle 1410 having a suitable shape and diameter, the diameter of the puncturing point can be controlled to be about 0.7 mm.

Figure 9:
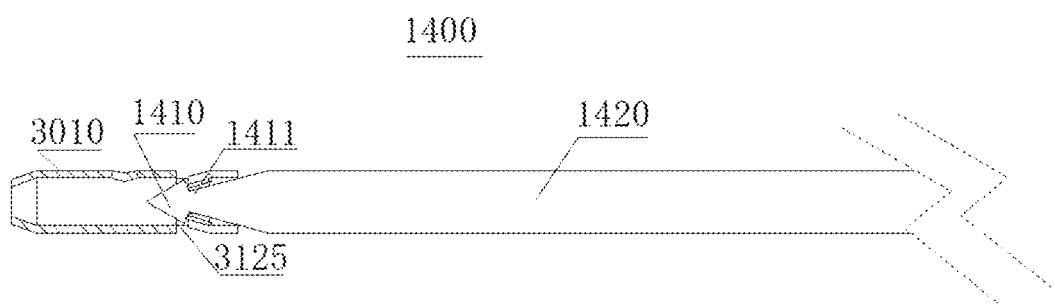
FIG. 9 is a schematic structural view illustrating a puncturing needle of a puncturing assembly of the suture implanting apparatus illustrated in FIG. 6 being coupled with a fixing member of the suture.

The puncturing needle 1410 is coupled to the fixing member 3010 through a non-detachable or detachable fixing connection manner A number of connection manners may be employed, for example, screw connection, bonding, rough-surface frictional connection, interference fit, or snap connection. In this implementation, the snap connection is used. Specifically, the fixing member 3010 defines at least one recess or at least one hole on an inner surface of the fixing member 3010. The at least one recess or hole is engaged with at least one protrusion or flange of the puncturing needle 1410. As illustrated in FIG. 9, the fixing member 3010 defines three recesses 3125 on the inner surface thereof along a radial direction of the fixing member 3010. The three recesses 3125 are engaged with flanges 1411 of the puncturing needle 1410. With the three recesses 3125, not only stability between the fixing member 3010 and the puncturing needle 1410 can be ensured and swinging amplitude of the puncturing needle 1410 can be reduced, but also the diameter of the puncturing point is not increased due to that the diameter of the puncturing needle 1410 is not additionally increased.

As illustrated in FIG. 7, a proximal end of the puncturing needle 1410 is coupled to the puncturing push rod 1420. The puncturing push rod 1420 is movably received in the lumen of the pushing shaft 1210. A proximal end of the puncturing push rod 1420 extends out of the proximal end of the pushing shaft 1210 and then is coupled with a third handle 1401. Therefore, an axial movement of the third handle 1401 can drive the puncturing push rod 1420 to move along an axial direction of the pushing shaft 1210, thereby driving the puncturing needle 1410 toward the distal end to perform puncturing or drawing back the puncturing needle 1410 toward the proximal end. After the leaflet is clamped by the clamping assembly 1300, the puncturing needle 1410 can be driven by the third handle 1401 to puncture the leaflet and is then coupled with the fixing member 3010 of the suture 3000. In the related art, a rate of hooking the suture 3000 by the hooked needle is relatively low, thereby reducing an operation successful rate and prolonging operation time. Furthermore, after hooking the suture 3000, since the needle is coupled with the suture 3000 merely through a relatively small friction force, during drawing back the needle, due to patient's blood flow or actions of the operator, the suture 3000 may slip off the needle, thereby resulting in failure of surgery. However, in this implementation, the puncturing needle 1410 is stable and reliably coupled with the fixing member 3010 of the suture 3000, and the suture 3000 is not easily detached from the fixing member 3010, and thus the operator can conveniently and quickly draw back one or two ends of the suture 3000 coupled with the fixing members 3010.

Referring to FIGS. 6-8, the clamping assembly 1300 includes a clamping push rod 1330 for receiving the suture 3000, a distal clamp 1310, and a proximal clamp 1320. The distal clamp 1310 and the proximal clamp 1320 can open and close relatively to clamp the leaflet. The clamping push rod 1330 is movably received in the pushing shaft 1210. The distal clamp 1310 is disposed at a distal end of the clamping push rod 1330. The proximal clamp 1320 is disposed at the distal end of the pushing shaft 1210. A proximal end of the clamping push rod 1330 extends out of the proximal end of the pushing shaft 1210 and is coupled with a second handle 1301. The distal clamp 1310 and the proximal clamp 1320 opening and closing relatively means that the distal clamp 1310 and the proximal clamp 1320 move relative to each other to form an open state or a close state. The second handle 1301 is pushed toward the distal end to drive the clamping push rod 1330 to move toward the distal end, so that the distal clamp 1310 moves away from the proximal clamp 1320 to form the open state illustrated in FIG. 8. At this point, the distal clamp 1310 and the proximal clamp 1320 can cooperatively define a receiving space for receiving the leaflet. When the leaflet enters the receiving space, the second handle 1301 is drawn back toward the proximal end, such that the distal clamp 1310 moves close to the proximal clamp 1320 to form the close state illustrated in FIG. 6. At this point, the leaflet is clamped and fixed by the clamping assembly 1300. The shapes of the proximal clamp 1320 and the distal clamp 1310 need to be adapted to the shape of the pushing shaft 1210. The distal clamp 1310 and the proximal clamp 1320 in the close state need to form a smooth overall appearance to facilitate pushing and reducing damage to the patient. It is to be understood that pushing the second handle 1301 toward the distal end to cause the distal clamp 1310 to be away from the proximal claim 1320 can be realized via drawing back the first handle 1201 and the pushing shaft 1210 toward the proximal end, and drawing back the second handle 1301 toward the proximal end to cause the distal clamp 1310 to be close to the proximal clamp 1320 can be realized via pushing the first handle 1201 and the pushing shaft 1210 toward the distal end.

It is to be understood that in other implementations, the proximal clamp 1320 that is set separately may be omitted, and the distal end of the pushing shaft 1210 may be directly used as the proximal clamp 1320 to cooperate with the distal clamp 1310 to clamp the leaflet. In this implementation, the pushing shaft 1210 is preferably a rod-shaped body defining multiple lumens that are spaced apart from each other, and a distal surface of the rod-shaped body acts as a clamping surface for clamping the leaflet.

In order to improve the stability of the clamping, a clamping surface of the proximal clamp 1320 (i.e., a distal surface of the proximal clamp 1320) needs to abut against a clamping surface of the distal clamp 1310 (i.e., a proximal surface of the distal clamp 1310) to clamp the leaflet. The clamping surface of the proximal clamp 1320 and the clamping surface of the distal clamp 1310 each have a relatively large leaflet contact area. For example, the clamping surface of the proximal clamp 1320 and the clamping surface of the distal clamp 1310 may both be inclined, that is, the clamping surface of the proximal clamp 1320 and the axial direction of the pushing shaft 1210 cooperatively define an angle smaller than 90 degrees, i.e., an acute angle, and the clamping surface of the distal clamp 1310 and the axial direction of the pushing shaft 1210 cooperatively define an angle smaller than 90 degrees, i.e., an acute angle. Furthermore, the distal clamp 1310 is provided with a clamping reinforcement member for increasing a clamping force on the clamping surface of the distal clamp 1310, and/or the proximal clamp 1320 is provided with a clamping reinforcement member for increasing a clamping force on the clamping surface of the proximal clamp 1320. The clamping reinforcement member is preferably at least one of a projection, a rib, a groove or a recess. The shape of the clamping reinforcement member on the clamping surface of the distal clamp 1310 needs to be adapted to the shape of the clamping reinforcement member on the clamping surface of the proximal clamp 1320, such that there is no gap between the distal clamp 1310 and the proximal clamp 1320 when the distal clamp 1310 and the proximal claim 1320 are in the close state. In this implementation, multiple ribs protrude in parallel from the clamping surface of the distal clamp 1310 and the clamping surface of the proximal clamp 1320 and act as the clamping reinforcement members, and when the distal clamp 1310 and the proximal clamp 1320 are in the close state, there is no gap between the distal clamp 1310 and the proximal clamp 1320.

Figure 10A:
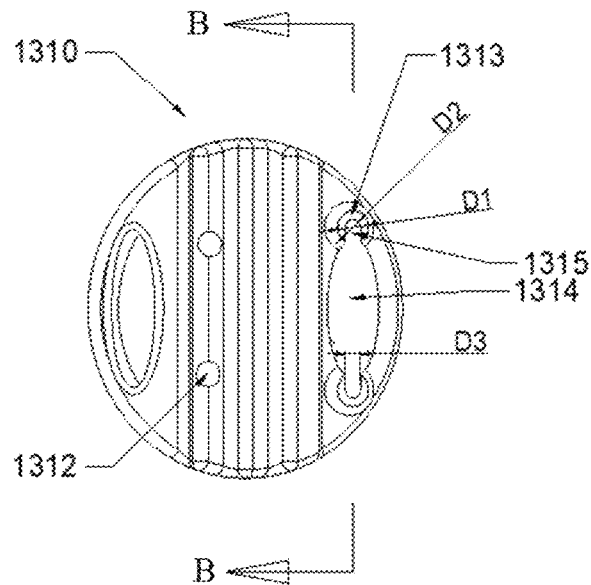
FIG. 10A is a schematic structural view illustrating a proximal clamp of the suture implanting apparatus illustrated in FIG. 6.
Figure 10B:
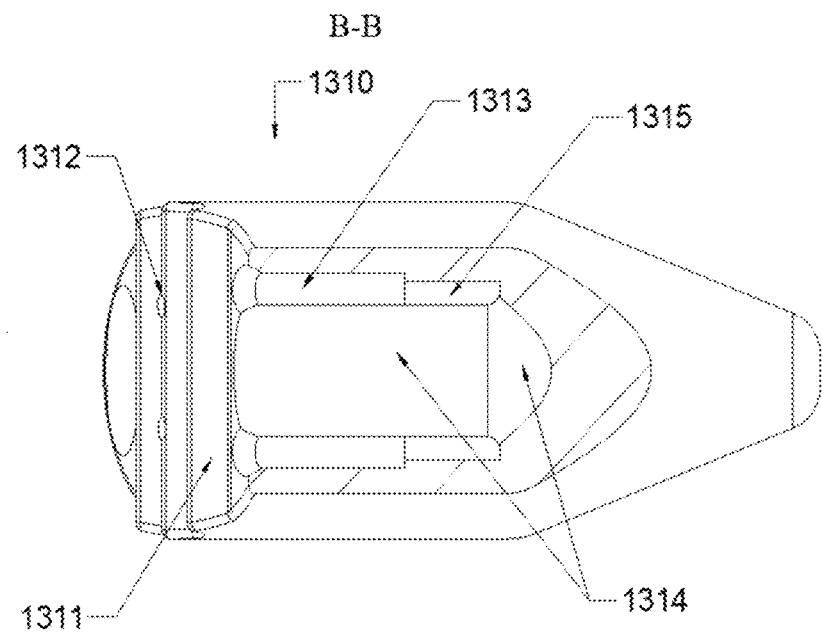
FIG. 10B is a cross-sectional view of the proximal clamp illustrated in FIG. 10A, taken along line B-B.

The clamping push rod 1330 is a tubular body or a hollow rod-shaped body with a certain axial length. Referring to FIG. 10A and FIG. 10B together, a cross section of the clamping push rod 1330 is preferably elliptical, semicircular, crescent, circular, or the like. The clamping push rod 1330 defines a suture channel 1331 along an axial direction of the clamping push rod 1330. The distal clamp 1310 defines two suture receiving spaces 1315 respectively communicating with the suture channel 1331. The two suture receiving spaces 1315 respectively extend through the distal clamp 1310 and reach the clamping surface of the distal clamp 1310. The suture 3000 is received in the suture channel 1331 and the two suture receiving spaces 1315.

The distal clamp 1310 defines two fixing cavities 1313 on the clamping surface thereof to accommodate the two fixing members 3010 of the suture 3000, respectively. Each fixing cavity 1313 axially communicates with one suture receiving cavity 1315. The positions of the two fixing cavities 1313 correspond to the positions of the two puncturing needles 1410, respectively. Thus, the two fixing members 3010 of the suture 3000 are respectively accommodated in the distal clamp 1310, and the proximal end of each fixing member 3010 corresponds to one puncturing needle 1410.

In this implementation, the suture 3000 is placed and fixed in the instrument, thereby avoiding that the suture 3000 rubs tissues to damage the tissues during that the suture 3000 is driven into the patient's body by the instrument, and further avoiding leakage of blood around the suture 3000. In addition, the distance between the fixing cavity 1313 and the clamping push rod 1330 is the distance between the suture 3000 implanted and the edge of the leaflet, thereby effectively avoiding folding of the edge of the leaflet or a notch of the mitral valve, and accordingly the surgical effect is improved.

Referring to FIGS. 10A-10B, since the anti-slip member 3020 is sleeved on the suture 3000, the distal clamp 1310 further defines a receiving groove 1314 on the clamping surface thereof to receive the anti-slip member 3020. The receiving groove 1314 radially communicates with the two suture receiving cavities 1315, respectively. Therefore, after the two puncturing needles 1410 respectively puncture the leaflet and are respectively coupled with the fixing members 3010, the two puncturing push rods 1420 are drawn back to pull the two puncturing needles 1410, the two fixing members 3010 respectively coupled with the two puncturing needles 1410, the suture 3000, and the anti-slip member 3020 out of the clamping surface of the distal clamp 1310 sequentially, until the two puncturing needles 1410, the two fixing members 3010, and the suture 3000 pass through the leaflet sequentially and the anti-slip member 3020 abuts against the upper surface of the leaflet.

With the fixing cavity 1313 and the receiving groove 1314, the suture 3000 and the anti-slip member 3020 can be pulled to the leaflet without releasing the distal clamp 1310 and the proximal clamp 1320. Therefore, during changing the state of the distal clamp 1310 and the proximal clamp 1320 from the close state to the open state, at the moment the leaflet slips off the clamping assembly 1300 and pulsating recoveries, the suture 3000 is not in contact with the leaflet alone, thereby preventing linear cutting of the suture 3000 from damaging the pulsatile leaflet.

With the fixing cavity 1313, not only the fixing member 3010 of the suture 3000 can be fixed in the fixing cavity 1313, but also the fixing member 3010 can be pulled out of the fixing cavity 1313 by an external force. Therefore, the shape of the fixing cavity 1313 is adapted to the shape of the fixing member 3010, and a diameter of an inscribed circle of the fixing cavity 1313 is larger than a diameter of a circumscribed circle of the suture receiving cavity 1315. Preferably, a ratio of the diameter of the circumscribed circle of the suture receiving cavity 1315 to the diameter of the inscribed circle of the fixing cavity 1313 falls within a range from 0.2:1 to 0.4:1. When a cross section of the fixing cavity 1313 and a cross section of the suture receiving cavity 1315 are both circular, the diameter of the inscribed circle of the fixing cavity 1313 equals the diameter of the circular cross section of the fixing cavity 1313, and the diameter of the circumscribed circle of the suture receiving cavity 1315 equals the diameter of the circular cross section of the suture receiving cavity 1315. In this implementation, the cross section of the fixing cavity 1313 is circular, and the diameter of the fixing cavity 1313 is D1. The cross section of the suture receiving cavity 1315 is circular, and the diameter of the suture receiving cavity 1315 is D2, where D2 is 30% of D1. The purpose of such setting is as follows. If D2 is too large, during driving the puncturing needle 1410 by the puncturing push rod 1420 to be engaged with the fixing member 3010 of the suture 3000, due to the pushing force that is generated by the puncturing push rod 1420 and for pushing the puncturing needle 1410 toward the distal end, the fixing member 3010 may slide out of the fixing cavity 1313 and enter the suture receiving cavity 1315, and thus the puncturing needle 1410 cannot be successfully coupled with the fixing member 3010 of the suture 3000 at a time, thereby prolonging the operation time. If D2 is too small, the fixing member 3010 of the suture 3000 cannot smoothly pass through the suture receiving cavity 1315, and thus after the puncturing needle 1410 is coupled with the fixing member 3010 of the suture 3000, the suture 3000 cannot be smoothly pulled out of the clamping surface of the clamping push rod 1330. It is to be understood that, in other implementations, the cross section of the fixing cavity 1313 and the cross section of the suture receiving cavity 1315 may be in the shape of an ellipse, a triangle, a square, a polygon, or the like, and what is needed is that the shape of the fixing cavity 1313 is adapted to the shape of the fixing member 3010 and the suture 3000 can smoothly pass through the suture receiving cavity 1315.

In order to smoothly pull the suture 3000 and the anti-slip member 3020 out of the clamping surface of the distal clamp 1310, the fixing cavity 1313 and the receiving groove 1314 radially communicate with each other. Preferably, a width D3 of a connecting portion between the fixing cavity 1313 and the receiving groove 1314 falls within a range from 20% of D1 to 50% of D1. The purpose of such settings is as follows. If D3 is too large, the fixing member 3010 of the suture 3000 cannot be fixedly hold in the fixing cavity 1313 of the distal clamp 1310 and easily slides out of the fixing cavity 1313, thereby causing failure of the instrument. If D3 is too small, after the puncturing needle 1410 is coupled with the fixing member 3010 of the suture 3000, the fixing member 3010 cannot be smoothly pulled out of the fixing cavity 1313, thereby resulting in operation failure.

Figure 11A:
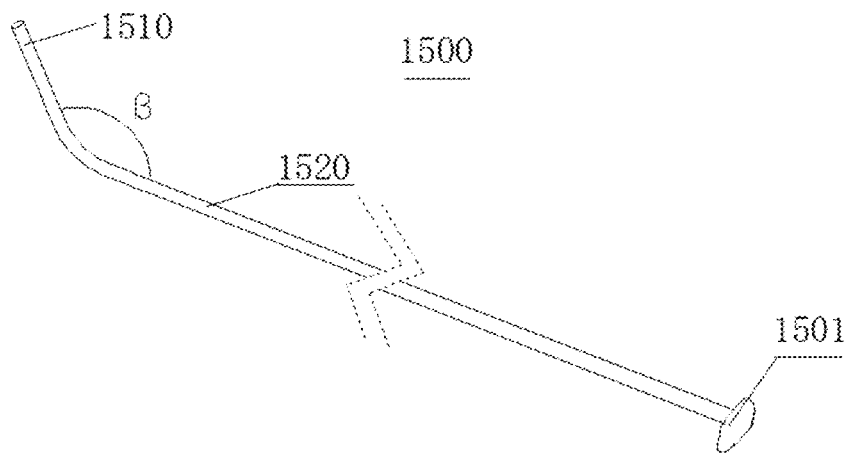
FIGS. 11A-11B are schematic structural views illustrating clamping auxiliary assemblies of the suture implanting apparatus illustrated in FIG. 6 according to different implementations.
Figure 11B:
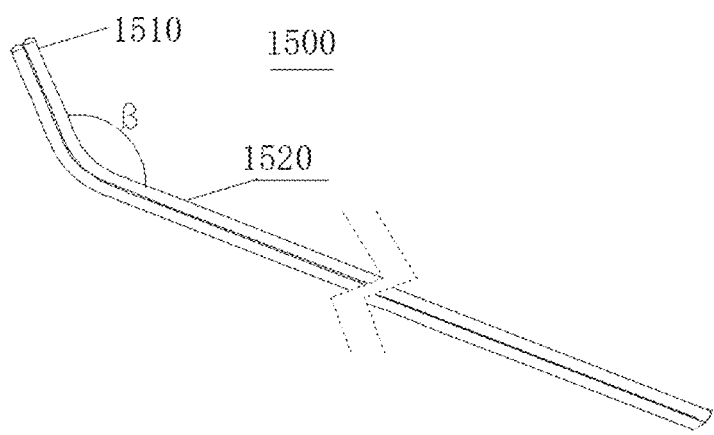

Referring back to FIG. 7, to further enhance the clamping, the suture implanting apparatus 1000 further includes a clamping auxiliary assembly 1500. As illustrated in FIG. 11A and FIG. 11B, the clamping auxiliary assembly 1500 includes at least one clamping auxiliary arm 1520 movably received in the pushing shaft 1210 and at least one clamping auxiliary member 1510 each disposed at a distal end of one clamping auxiliary arm 1520. In order to facilitate the pushing, the clamping auxiliary arm 1520 is also provided with a fourth handle 1501 at a proximal end thereof.

Figure 12:
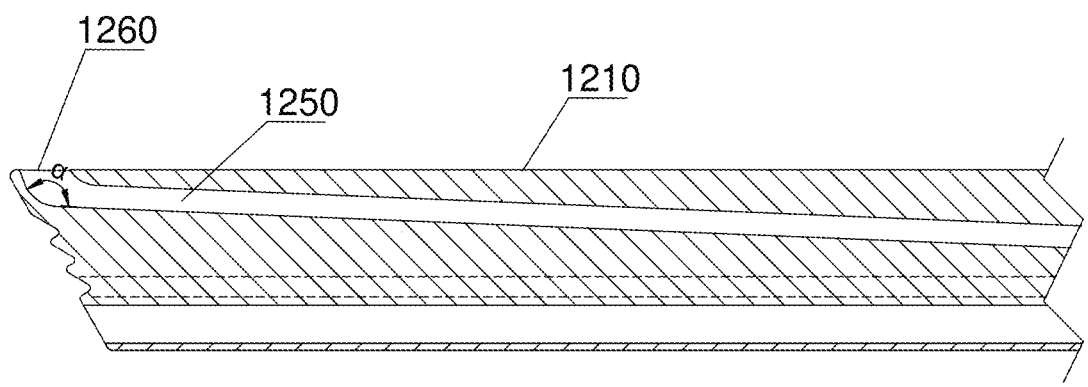
FIG. 12 is a cross-sectional view of a distal end of a pushing shaft of the suture implanting apparatus illustrated in FIG. 6, taken along an axial direction of the pushing shaft.
Figure 13A:
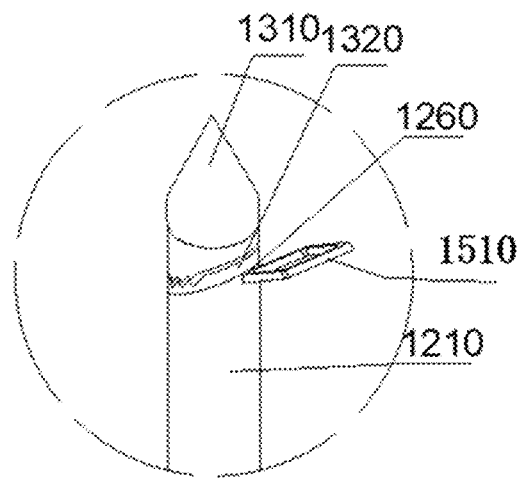
FIGS. 13A-13B are schematic structural views illustrating the clamping auxiliary assembly locating below a lower surface of a leaflet to support the leaflet.
Figure 13B:
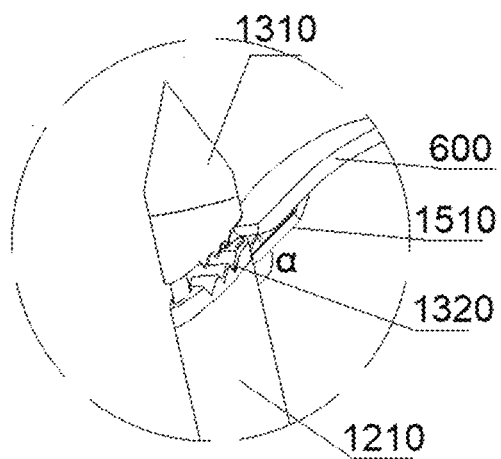

As illustrated in FIG. 12, the pushing shaft 1210 defines an auxiliary arm receiving cavity 1250 along an axial direction thereof. Before puncturing, the clamping auxiliary member 1510 and the clamping auxiliary arm 1520 are both received in the auxiliary arm receiving cavity 1250. An opening 1260 is defined on the clamping surface of the proximal clamp 1320, the sidewall of the pushing shaft 1210, or the sidewall of the proximal clamp 1320. The opening 1260 communicates with the auxiliary arm receiving cavity 1250. When the fourth handle 1501 is pushed toward the distal end by the operator, the clamping auxiliary arm 1520 can be driven to push the clamping auxiliary member 1510 out of the opening 1260 (as illustrated in FIG. 13A), and then the clamping auxiliary member 1510 locates below a lower surface of the leaflet 600 to support the leaflet 600, and thus the pulsatile leaflet 600 is stabilized, a movement amplitude of the leaflet 600 is reduced, and the clamping auxiliary member 1510 cooperates with the clamping assembly 1300 to clamp and fix the leaflet 600 (as illustrated in FIG. 13B)

An included angle α between an axial direction of a distal end of the auxiliary arm receiving cavity 1250 and the axial direction of the pushing shaft 1210 ranges from 120 degrees to 150 degrees. The reason for such setting is as follows. Before puncturing, the clamping push rod 1330 is in contact with the edge of the leaflet, and the distal clamp 1310 and the proximal clamp 1320 can only clamp part of the leaflet. In this case, in order to keep the pulsatile leaflet be stable and make the pulsate leaflet be easy to be punctured, it is necessary to provide support for the other side opposite the edge of the leaflet, and thus a certain included angle needs to be defined between the clamping auxiliary member 1510 passing through the opening 1260 and the pushing shaft 1210, so as to enable the clamping auxiliary member 1510 to locate below the lower surface of the leaflet at the other side opposite the edge of the leaflet to support the leaflet. An included angle between the clamping auxiliary member 1510 and the pushing shaft 1210 is substantially equal to the included angle α between the axial direction of the distal end of the auxiliary arm receiving cavity 1250 and the axial direction of the pushing shaft 1210.

The clamping auxiliary member 1510 has a rod-shaped structure formed by at least one support rod. The clamping auxiliary member 1510 is made from a biocompatible elastic and/or flexible material to be adapted to an anatomical structure and a movement amplitude of the leaflet and avoid damage to the leaflet. The elastic material is preferably a shape memory material. The clamping auxiliary member 1510 may be made from a metallic material, a polymeric material, or a metal-polymer composite material. The support rod may have a solid or hollow structure of a single layer or multiple layers, or may be formed by winding a single wire or multiple wires. The cross section of the support rod may be in the shape of a circle, an ellipse, a crescent, a semicircle, a polygon, or the like. The clamping auxiliary member 1510 is smooth, and the distal end of the clamping auxiliary member 1510 is a smooth and round tip formed by spot welding, and there is no burr, no edge, no corner, or the like. In this implementation, the clamping auxiliary member 1510 is a support rod made from nickel-titanium alloy and has a circular cross section.

The clamping auxiliary arm 1520 is a rod or tube with a certain axial length and has a certain hardness or rigidity to provide supportability and push ability. The clamping auxiliary arm 1520 may be a metal rod or a polymer rod having a hollow or solid structure of a single layer or multiple layers, or may be formed by winding a single wire or multiple wires. The cross section of the clamping support arm 1520 may be in the shape of a circle, an ellipse, a crescent, a semicircle, a polygon, a ring, or the like. The clamping auxiliary arm 1520 may be made from a metal material, a polymer material, or a metal-polymer composite material.

Figure 14A:
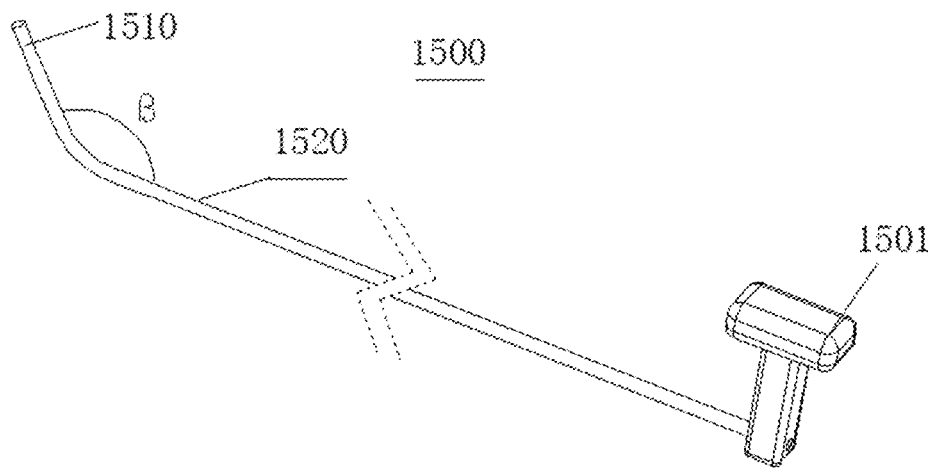
FIGS. 14A-14G are schematic structural views illustrating clamping auxiliary assemblies according to different implementations.

The supportability of the clamping auxiliary arm 1520 and the flexibility of the clamping auxiliary member 1510 can be achieved by using different materials to manufacture the clamping auxiliary member 1510 and the clamping auxiliary arm 1520, respectively, that is, the clamping auxiliary arm 1520 is made of a rigid material, and the clamping auxiliary member 1510 is made of an elastic and/or flexible material. It can be understood that the clamping auxiliary arm 1520 and the clamping auxiliary member 1510 may be made of the same material, and a material having a relatively hardness is added outside or inside the clamping auxiliary arm 1520 to act as a reinforcing tube or a stiffened wire to ensure the supportability of the clamping auxiliary arm 1520 (as illustrated in FIG. 14A). Preferably, the clamping auxiliary arm 1520 and the clamping auxiliary member 1510 define an included angle β ranging from 120 degrees to 150 degrees.

The clamping auxiliary member 1510 is at least partially made from a radiopaque material. In the related art, before the clamping assembly clamps the leaflet, a relative position between the instrument and the leaflet cannot be determined by means of an operation of a low level such as X-rays, the clamping assembly is moved to a suitable position by means of precise ultrasonic guidance, and the pulsatile state of the leaflet is observed by ultrasonography. When the leaflet pulsates and gets close to the clamping assembly, the relative movement between the distal clamp and the proximal clamp is quickly driven to clamp the leaflet. Ultrasonography has high requirements for doctors' operation techniques and capability of analyzing cardiac ultrasonography, resulting in increased surgical cost, surgical difficulty, and surgical time. In the implementation, the clamping auxiliary member 1510 is made from the radiopaque material. After the clamping auxiliary member 1510 is in contact with the leaflet, the flexible and/or elastic clamping auxiliary member 1510 produces a corresponding swing following movement of the leaflet, so that the operator can quickly and accurately determine the position of the leaflet by X-rays before the clamping assembly 1300 clamps the leaflet. Therefore, the clamping assembly 1300 can be operated to clamp the leaflet quickly and accurately, thereby reducing the operation cost and difficulty, shortening the surgical time, and improving the surgical success rate.

Figure 14B:
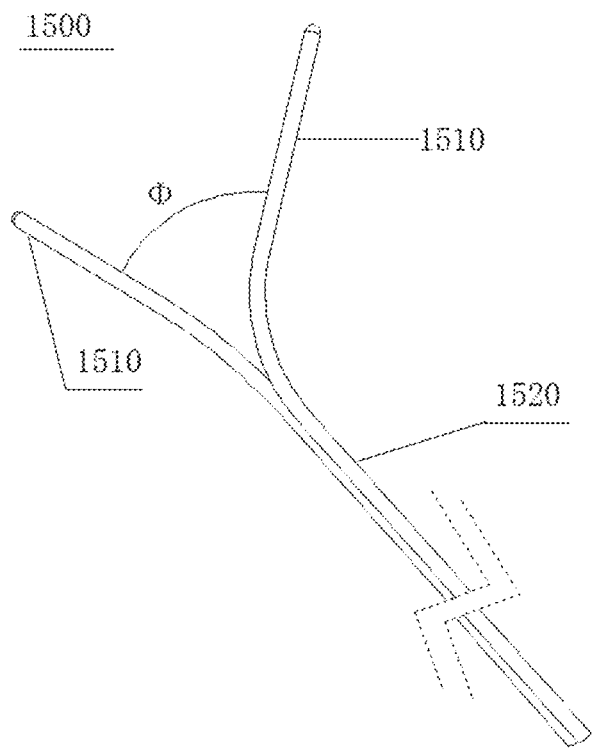

It is to be understood that, in other implementations, in order to enhance the strength of the clamping auxiliary assembly 1500, the clamping auxiliary member 1510 may also have a deformed structure formed by multiple support rods. After the clamping auxiliary member 1510 having the deformed structure is contracted and deformed, the clamping auxiliary member 1510 and the clamping auxiliary arm 1520 are both received in the pushing shaft 1210. As illustrated in FIG. 14B, the deformed structure is an open bifurcated structure or an umbrella-like structure formed by multiple support rods, and an included angle co of the bifurcated structure is smaller than or equal to 150 degrees. In order to facilitate being pushed in the pushing shaft 1210, the clamping auxiliary member 1510 can be switched between a contracted state and a naturally stretched state. When the clamping auxiliary member 1510 is in the contracted state, the clamping auxiliary member 1510 can be accommodated in the auxiliary arm receiving cavity 1250 of the pushing shaft 1210 and pushed. When the clamping auxiliary member 1510 extends out of the opening 1260, the clamping auxiliary member 1510 is switched to be in the stretched state to locate below the lower surface of the leaflet, so as to support and stabilize the pulsatile leaflet. The contact surface between the clamping auxiliary member 1510 having a large diameter and the leaflet is a plane where the clamping auxiliary member 1510 locates. Therefore, there is a relatively large contact area between the clamping auxiliary member 1510 and the leaflet, and thus the clamping auxiliary member 1510 can well abut against the leaflet to improve the supportability of the clamping auxiliary assembly 1500.

Figure 14C:
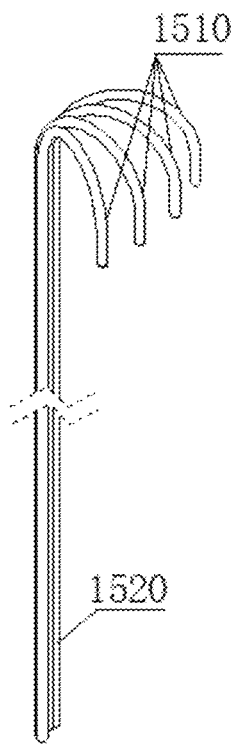

It is to be noted that, in other implementations, the distal ends of the clamping auxiliary member 1510 having the open bifurcated structure or the umbrella-like structure may be rolled up toward the proximal end of the clamping auxiliary arm 1520. Multiple clamping auxiliary members 1510 form a recessed area, as illustrated in FIG. 14C. At this point, since the distal ends of each clamping auxiliary member 1510 are rolled up inwardly and point toward the proximal end of the clamping auxiliary arm 1520, the distal end of the support rod of the clamping auxiliary member 1510 can be prevented from puncturing the leaflet or the ventricular wall.

Figure 14D:
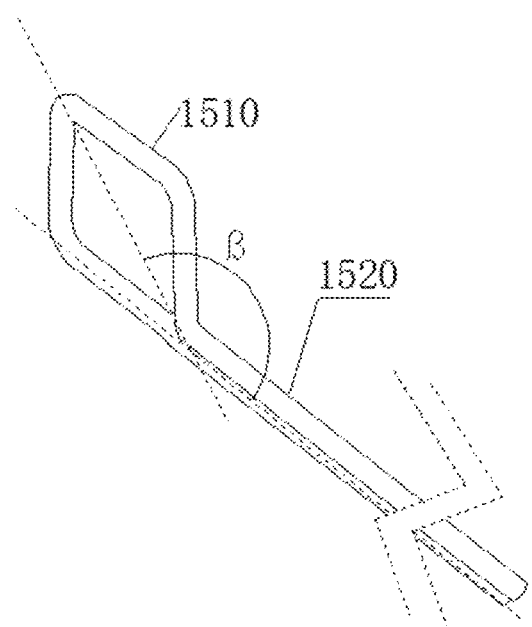
Figure 14E:
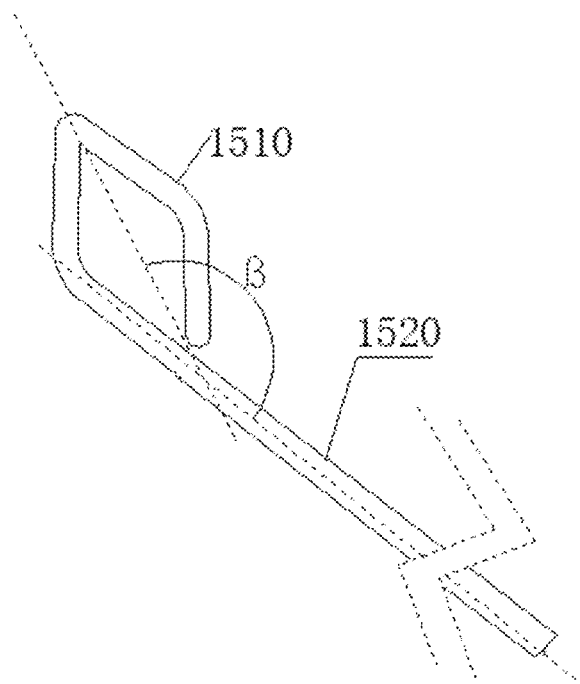
Figure 14F:
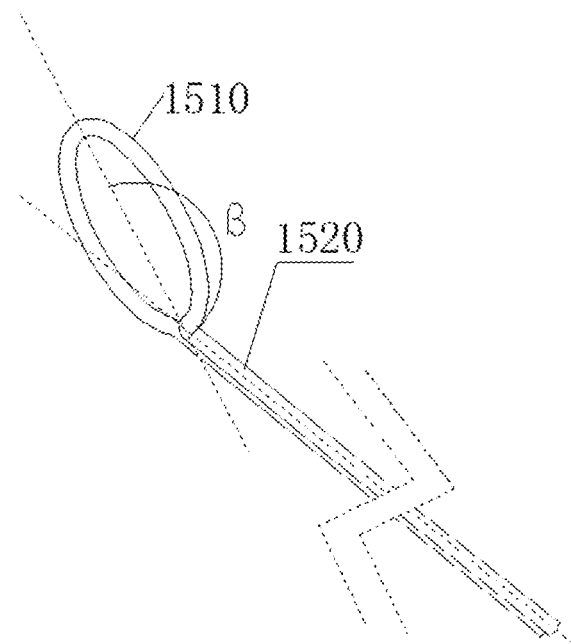
Figure 14G:
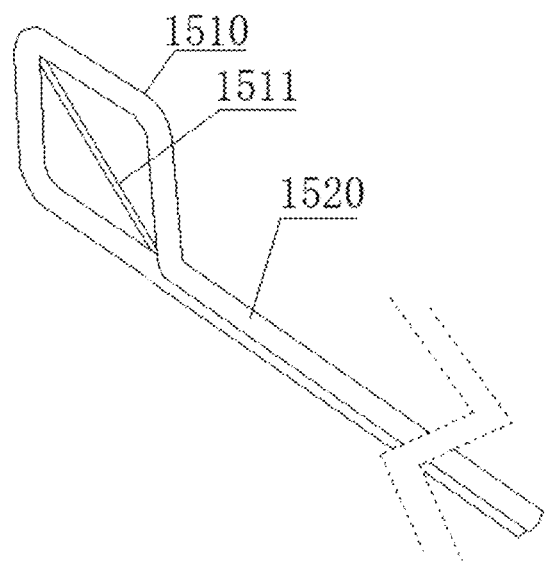

As illustrated in FIGS. 14D-14F, it is to be understood that, in other implementations, the deformed structure may also be a closed-loop structure formed by multiple support rods. The closed-loop structure may be in the shape of a circle, a diamond, an ellipse, a pear, a polygon or may have other irregular shapes that may form a close structure. Referring to FIG. 14G, it is to be understood that, in other implementations, at least one flexible and/or elastic connecting rod 1511 may be disposed between the support rods forming the closed-loop structure to improve the stability of the closed-loop structure and further enhance the supportability of the clamping auxiliary member 1510 leaflet. It is to be understood that, in other implementations, when multiple support rods and connecting rods 1511 are used to form the closed-loop structure, the closed-loop structure may also be a sheet structure or a mesh structure. It is to be understood that, in other implementations, the mesh structure may also be subjected to heat-treatment processing to form a disc-shaped structure that may be stretchable and deformable, and the disc-shaped structure may be further subjected to the heat-treatment processing to form a columnar structure, a nested structure, an oblate structure, or the like. As long as the clamping auxiliary member 1510 is made from the shape memory material, the clamping auxiliary member 1510 can be received in the auxiliary arm receiving cavity 1250 of the pushing shaft 1210 to be delivered, and then the clamping auxiliary member 1510 extends out of the opening 1260 to return to a naturally unfolded state, so as to be in contact with the lower surface of the leaflet to support the leaflet. It can also be understood that, in other implementations, the clamping auxiliary member may also be a balloon with a flat surface, where the balloon may be inflated and expanded under pressure, and then locates below the lower surface of the leaflet to support the leaflet.

Figure 15A:
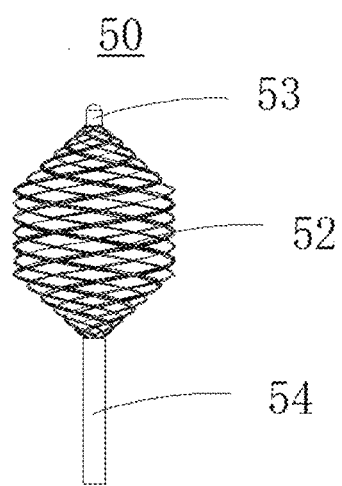
FIGS. 15A-15C are schematic structural views illustrating clamping auxiliary members of the clamping auxiliary assembly illustrated in FIG. 12 according to different implementations.
Figure 15B:
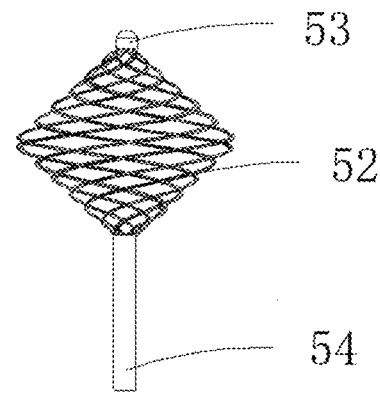
Figure 15C:
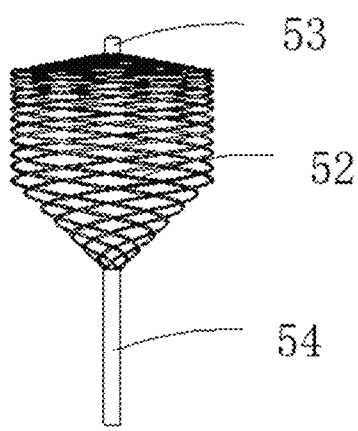

The clamping auxiliary member 1510 having the deformed structure may also include an elastic member 50 illustrated in FIGS. 15A-15C. The elastic member 50 is compressed to be in a compressed state along with that the clamping auxiliary arm 1520 is enabled to be received in the auxiliary arm receiving cavity 1250. When the elastic member 50 extends out of the auxiliary arm receiving cavity 1250 following the clamping auxiliary arm 1520, i.e., when the distal end of the clamping auxiliary arm 1520 extends beyond a free end of the auxiliary arm receiving cavity 1250, the elastic member 50 is no longer pressed by an external force and stretches to be in a stretched state. The area of the elastic member 50 in the stretched state is larger than that of the elastic member 50 in the compressed state, so that there is a relatively large area between the elastic member 50 and the leaflet, and the elastic member 50 can well abut against the leaflet to improve the ability that the clamping auxiliary arm 1520 supports the leaflet.

Specifically, the elastic member 50 is a deformable mesh cage, that is, the elastic member 50 has a cage-like structure formed by weaving wires with a certain elasticity and tension. When the mesh cage is received in the auxiliary arm receiving cavity 1250, the mesh cage is squeezed and deformed to be in a compressed state, so that the wires are deformed and gathered together, the volume of the mesh cage is reduced, and the mesh cage squeezed can be received in the auxiliary arm receiving cavity 1250. When the mesh cage extends out of the auxiliary arm receiving cavity 1250, the mesh cage stretches to be in a stretched state, the wire stretches to expand the mesh cage, and the volume of the stretched mesh cage is larger than the volume of the squeezed mesh cage, thereby providing relatively stable support for the leaflet supported by the clamping auxiliary arm 1520. In the present disclosure, the wires forming the mesh cage may be metal wires or elastic wires made from a polymer material. In this implementation, nickel-titanium wires are used, and the nickel-titanium wires have good biocompatibility and can be developed under X-rays, so that the position of the elastic member 50 can be quickly and accurately determined by X-rays. Further, compared with the clamping auxiliary member 1510 in the implementation illustrated in FIGS. 14A-14G, the elastic member 50 in this implementation has a three-dimensional structure, and thus a better three-dimensional development effect can be realized, and a relatively stable support can be provided for the leaflet supported by the clamping auxiliary arm 1520.

Referring to FIGS. 15A-15C together, in this implementation, the mesh cage includes a woven mesh 52, a head 53, and a fixing tube 54, where the head 53 and the fixing tube 54 are respectively fixed to two ends of the woven mesh 52. Specifically, the nickel-titanium wires form the woven mesh 52 in the shape of a cylinder. One end of the woven mesh 52 is fixed in the head 53, that is, with the head 53 one open end of the woven mesh 52 is gathered and fixed. The other end of the woven mesh 52 is gathered and fixed in the fixing tube 54. An end of the fixing tube 54 facing away from the woven mesh 52 is coupled to the clamping auxiliary arm 1520. Both the head 53 and the fixing tube 54 may be made of a metal material or a polymer plastic material. In this implementation, the head 53 is made of stainless steel, so that the position of the end of the elastic member 50 can be quickly and accurately determined by X-rays.

In this implementation, as illustrated in FIG. 15A, the mesh cage has a columnar middle part and two tapered ends, and taper angles of the two tapered ends are the same. It can be understood that, in the present disclosure, the mesh cage may also have any other shape. For example, the mesh cage may have a spindle-shaped structure with the same taper angle at both ends thereof illustrated in FIG. 15B, or may have a structure with different taper angles at both ends thereof illustrated in FIG. 15C.

Figure 16A:
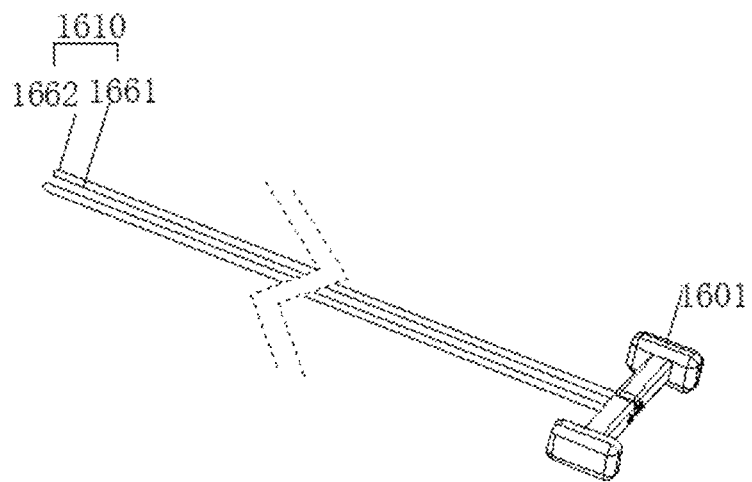
FIG. 16A is a schematic structural view illustrating a detecting assembly of the suture implanting apparatus illustrated in FIG. 6.

Referring back to FIG. 7, the suture implanting apparatus 1000 further includes a detecting assembly 1600. The detecting assembly 1600 is used to detect whether the leaflet is clamped between the distal clamp 1310 and the proximal clamp 1320. The detecting assembly 1600 includes at least one probe 1610. As illustrated in FIG. 16A, in this implementation, the detecting assembly 1600 includes two probes 1610 arranged in parallel. The distance between one of the two probes 1610 and the clamping push rod 1330 is substantially the same as that between the other of the two probes 1610 and the clamping push rod 1330.

Figure 16B:
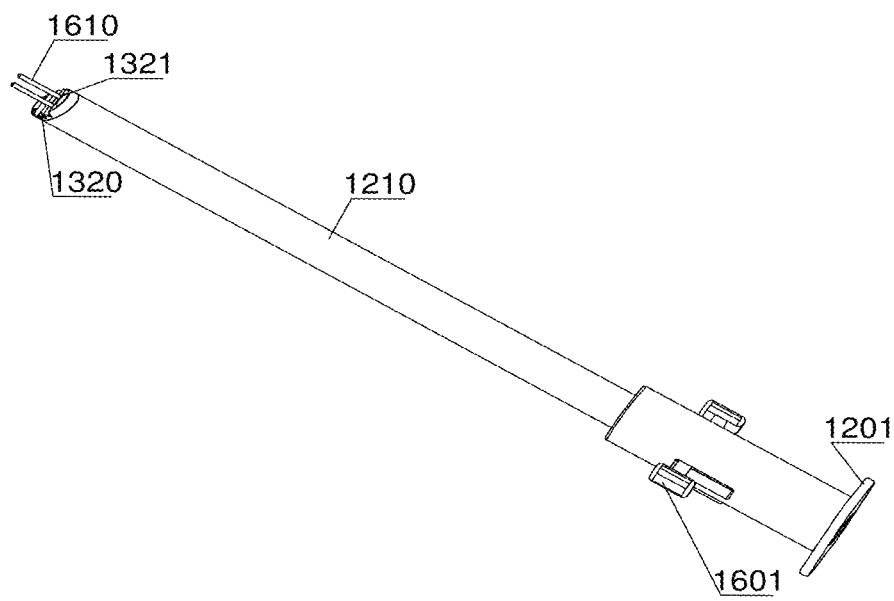
FIG. 16B is a schematic structural view illustrating the detecting assembly illustrated in FIG. 16A being received in the pushing shaft.
Figure 17:
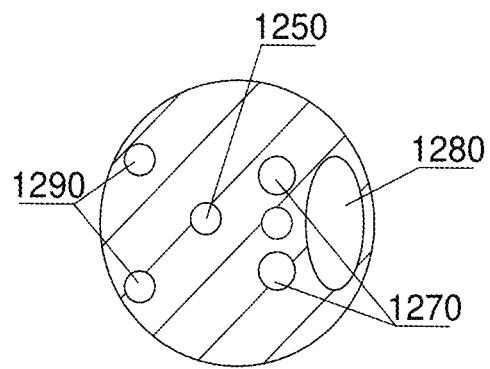
FIG. 17 is a cross-sectional view of the pushing shaft, taken along a radial direction of the pushing shaft.

As illustrated in FIG. 16B and FIG. 17, to ensure that the probe 1610 can extend out of the distal end of the pushing shaft 1210 to detect the leaflet, an axial length of the probe 1610 is preferably larger than a minimum axial length of the pushing shaft 1210. Each probe 1610 is movably received in one of probe channels 1270 defined in the pushing shaft 1210. For the sake of easy operation, a distal end of the probe 1610 is coupled with a detecting handle 1601. The clamping surface of the proximal clamp 1320 defines at least one probe outlet 1321 to enable that the distal end of the probe 1610 can extend out of the probe outlet 1321. The clamping surface of the distal clamp 1310 defines at least one probe receiving cavity 1312 corresponding to the at least one probe outlet 1321 and each used for receiving the distal end of one probe 1610. When the proximal clamp 1320 and the distal clamp 1310 are closed, the distal end of the probe 1610 extends out of the probe outlet 1321 and is received in the probe receiving cavity 1312.

As illustrated in FIG. 17, the pushing shaft 1210 defines the probe channels 1270, a clamping push rod channel 1280, and puncturing push rod channels 1290 in the axial direction thereof. The clamping push rod 1330 is installed in the clamping push rod channel 1280 of the pushing shaft 1210, each puncturing push rod 1420 is installed in one puncturing push rod channel 1290 of the pushing shaft 1210, and the axial directions of the clamping push rod 1330 and the puncturing push rod 1420 are both parallel to the axial direction of the pushing shaft 1210. The clamping push rod channel 1280 is defined at one side of the pushing shaft 1210, and the two puncturing push rod channels 1290 are defined at the other side of the pushing shaft 1210. The probe channels 1270 are arranged between the clamping push rod channel 1280 and the puncturing push rod channel 1290, and the distance between the probe channel 1270 and the clamping push rod channel 1280 is smaller than that between the probe channel 1270 and the puncturing push rod channel 1290. It can be understood that when the pushing shaft 1210 further defines the auxiliary arm receiving cavity 1250, the auxiliary arm receiving cavity 1250 is arranged between the clamping push rod channel 1280 and the puncturing push rod channel 1290, the probe channel 1270 is arranged between the clamping push rod channel 1280 and the auxiliary arm receiving cavity 1250, and the distance between the probe channel 1270 and the clamping push rod channel 1280 is smaller than that between the probe channel 1270 and the puncturing push rod channel 1290.

Figure 18A:
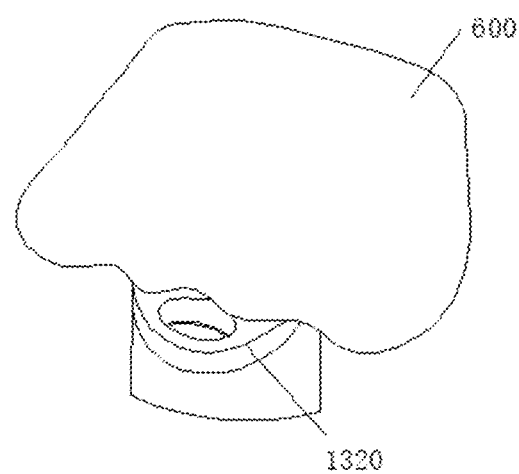
FIGS. 18A-18C are schematic views illustrating a detecting process performed by the detecting assembly.
Figure 18B:
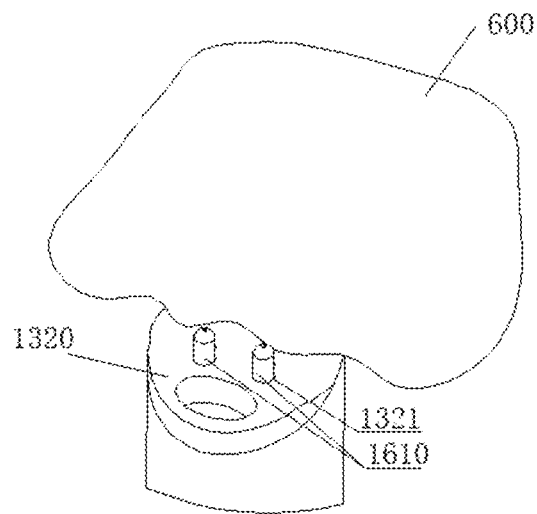
Figure 18C:
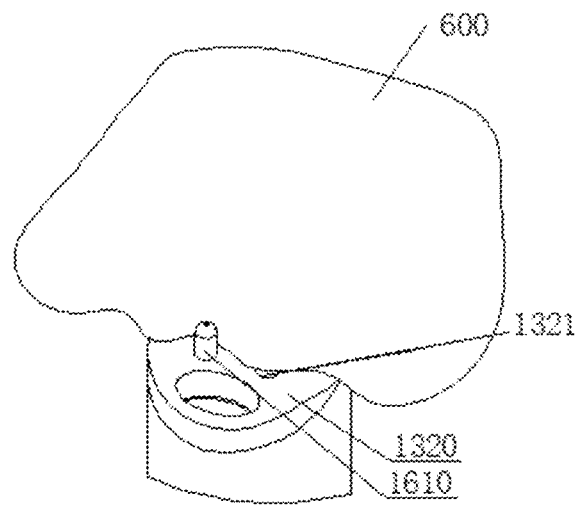

As illustrated in FIG. 18A, when the proximal clamp 1320 and the distal clamp 1310 are in the close state, if the leaflet 600 is clamped between the proximal clamp 1320 and the distal clamp 1310, and the edge of the leaflet 600 is in contact with the clamping push rod 1330, after the distal end of the probe 1610 extends out of the clamping surface of the proximal clamp 1320, further movement of the probe 1610 toward the distal end is blocked by the leaflet 600, which indicates that the leaflet 600 is well clamped and can be punctured. In addition, when the distal end of the probe 1610 is blocked by the leaflet 600 and cannot enter the probe receiving cavity 1312 illustrated in FIG. 10A, it also indicates that the relative position between the edge of the leaflet 600 and the suture 3000 is relatively fixed. As illustrated in FIG. 18B or FIG. 18C, if the leaflet 600 is not well clamped, that is, the leaflet 600 does not completely cover the probe outlet 1321 on the clamping surface of the proximal clamp 1320, the distal end of the probe 1610 can enter the probe receiving cavity 1312 on the distal clamp 1310 after extending out of the probe outlet 1321, and thus the operator needs to re-clamp the leaflet 600. Therefore, with the probe 1610 having a mechanical structure, the clamping of the leaflet 600 can be effectively detected, and the instrument has a simple structure and is easy to be operated.

As illustrated in FIG. 16A, the probe 1610 includes a probe body 1661 having a certain length and a probe end 1662 arranged at a distal end of the probe body 1661. The probe body 1661 and the probe end 1662 are integrally formed or fixedly coupled with each other. The probe body 1661 may have a solid or hollow structure. The cross section of the probe body 1661 may have a regular shape, such as may be in the shape of a circle, an ellipse, a crescent, a semicircle, a polygon, or the like, and may be preferably in the shape of a circle. The probe end 1662 has a solid or hollow structure with a smooth outer surface. For convenience of pushing, the shape of the probe end 1662 is selected from at least one of a cone shape, a table shape, a column shape, a sphere shape, or a hemisphere shape. Both the probe body 1661 and the probe end 1662 may be made of a metal material, a polymer material, or a metal-polymer composite material. For example, the probe body 1661 may have a solid rod-shaped or hollow tubular structure of a single layer or multiple layers, and may also be formed by winding a single wire or multiple wires.

The hardness of the distal end of the probe body 1661 is lower than or equal to that of the proximal end of the probe body 1661. That is, the distal end of the probe body 1661 preferably has flexibility or resilience to avoid that the leaflet is stabbed or damaged, and the proximal end of the probe body 1661 preferably has a certain hardness or stiffness to provide support and an ability of pushing.

The distal end and the proximal end of the probe body 1661 may be integrally formed or may be processed separately and then connected together in common technical manners in the related art such as welding, bonding, socketing, threading, or interference fit, or the like, that is, the support provided by the proximal end of the probe body 1661 and the flexibility of the distal end of the probe body 1661 can be achieved by using different materials to manufacture the proximal end and the distal end of the probe body 1661, respectively. It can be understood that, in other implementations, the whole rod body or tube body may be first made from a relatively soft material, and then an outer tube with a relatively high hardness is sleeved on the outer surface of the proximal end of the rod body or tube body to act as a reinforcement tube, so as to improve the support provided by the proximal end of the probe body 1661. Alternatively, a heat-shrinkable tube as a reinforcement tube is sleeved on the proximal end of the relatively soft rod body or tube body, and then the heat-shrinkable tube is heated and shrunk to be sleeved on the outer surface of the proximal end of the rod body or tube body to improve the support provided by the proximal end of the probe body 1661. It may also be understood that, for a rod body or tube body formed by winding a single wire or multiple wires, a thermoplastic elastomer such as Pebax and nylon can also be wrapped on the outer surface of the proximal end of the rod body or tube body, and then the thermoplastic elastomer is heated and melted to be wrapped on the outer surface and penetrate into gaps between multiple filaments or a single filament to improve the support provided by the proximal end of the probe body 1661.

It is to be understood that, in other implementations, the detecting assembly 1600 may include only one probe 1610, or may include multiple probes 1610. The multiple probes 1610 may be all received in one lumen of the pushing shaft 1210, i.e., the pushing shaft 1210 defines only one probe channel 1270. Alternatively, the multiple probes 1610 may be received in different lumens of the pushing shaft 1210, respectively, i.e., the pushing shaft 1210 defines multiple probe channels 1270.

Figure 19A:
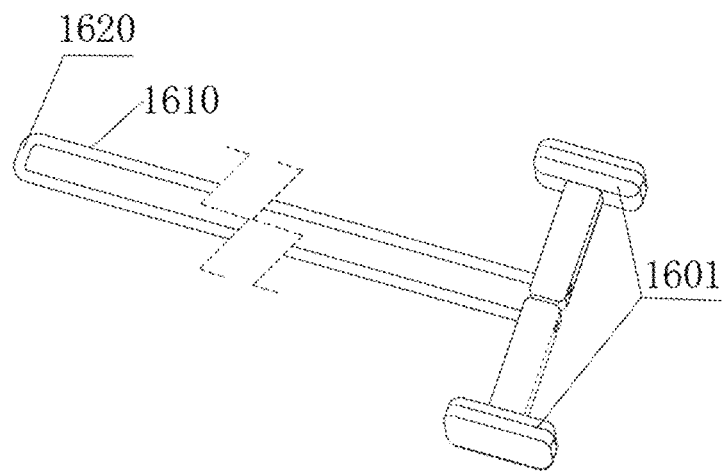
FIGS. 19A-19C are schematic structural views illustrating a detecting assembly according to another implementation.
Figure 19B:
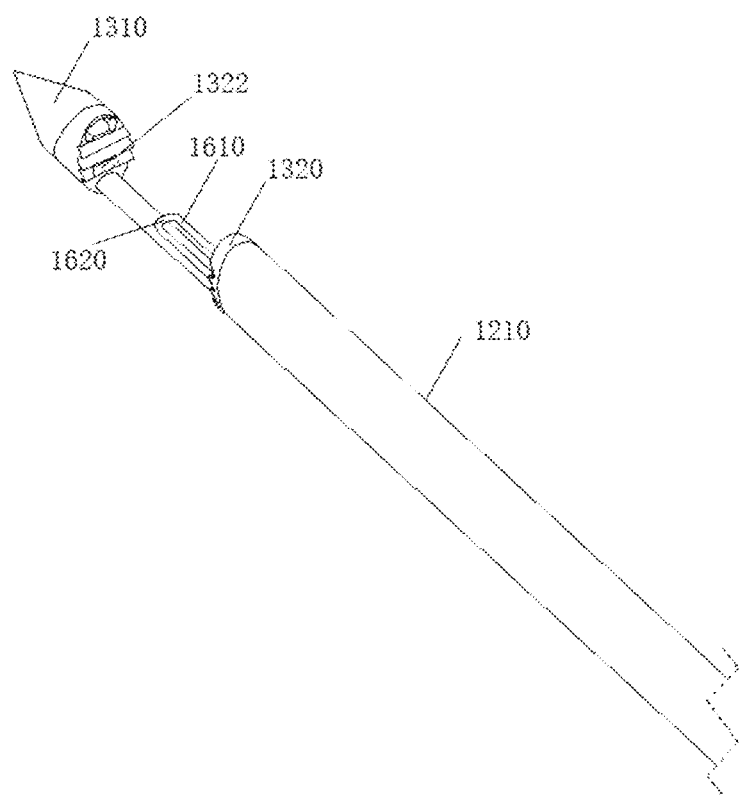
Figure 19C:
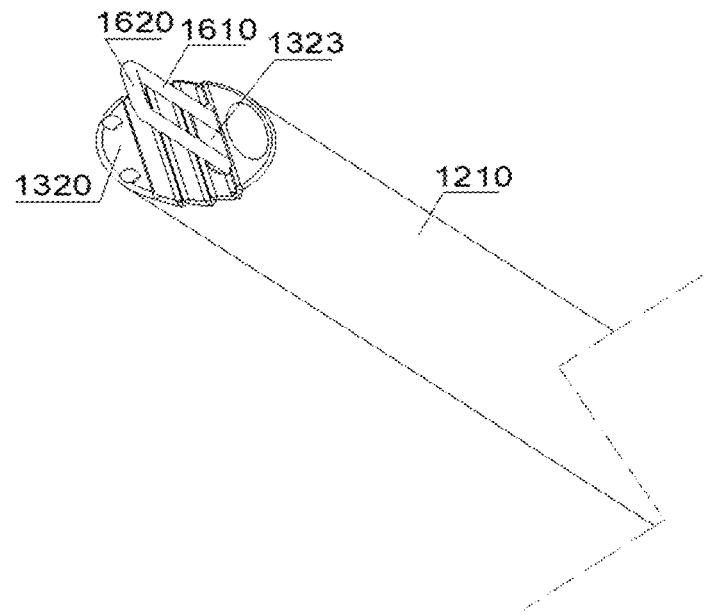

It is to be understood that, in other implementations, the distal ends of the probes 1610 can be coupled with each other. As illustrated in FIG. 19A, the distal ends of the probes 1610 have a certain elasticity/toughness and are coupled with each other via a connecting rod 1620. When the detecting handle 1601 is drawn back, the connecting rod 1620 is disposed on the clamping surface of the proximal clamp 1320. As illustrated in FIGS. 19B-19C, the clamping surface of the proximal clamp 1320 preferably defines a probe recess 1323 for receiving the connecting rod 1620. The probe recess 1323 needs to communicate with the probe channel 1270. Correspondingly, the clamping surface of the distal clamp 1310 defines a connecting rod receiving groove 1322 for receiving the connecting rod 1620. The connecting rod receiving groove 1322 respectively communicates with the two probe receiving cavities 1312. When the detecting handle 1601 of the detecting assembly 1600 is pushed toward the distal end, the distal ends of the two probes 1610 and the connecting rod 1620 all extend out of the proximal clamp 1320 and enter the connecting rod receiving groove 1322 and the probe receiving cavities 1312 of the distal clamp 1310. When the detecting handle 1601 is drawn back toward the proximal end, the distal ends of the two probes 1610 and the connecting rod 1620 are all drawn back from the distal clamp 1310, the distal ends of the probes 1610 are received in the probe channels 1270 of the pushing shaft 1210, and the connecting rod 1620 is disposed on the clamping surface of the proximal clamp 1320 or received in the probe recess 1323 on the clamping surface of the proximal clamp 1320.

Figure 20:
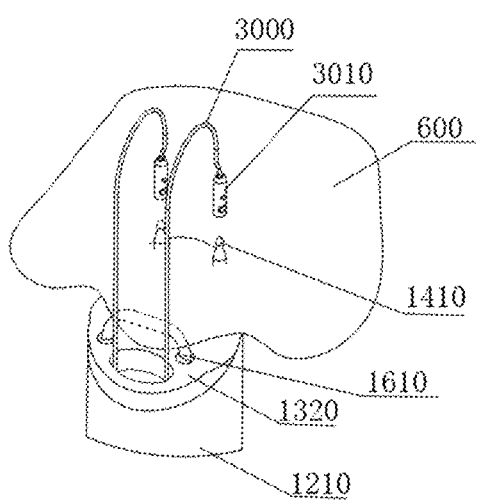
FIG. 20 is a schematic view illustrating a detecting process performed by the detecting assembly illustrated in FIGS. 19A-19C.

With regard to the detecting assembly 1600 in this implementation, since the contact area between the distal end of the detecting assembly 1600 and the leaflet is increased, the detecting assembly 1600 is particularly suitable for detecting the leaflet having an irregular shape. For example, as illustrated in FIG. 20, since the edge of the leaflet 600 is irregular, even if the leaflet 600 has been effectively clamped by the clamping assembly 1300, the leaflet 600 may just not cover the probe outlet 1321 of the proximal clamp 1320. However, in the implementation, the distal ends of the two probes 1610 are coupled together via the connecting rod 1620, the contact area between the distal end of the detecting assembly 1600 and the leaflet is accordingly increased, and thus the clamping of the leaflet can be detected, and then the operator performs puncturing of the leaflet and implants the suture 3000.

After the suture 3000 is implanted into the leaflet using the above suture implanting apparatus 1000, the suture 3000 is fixed by the suture locker 2000.

Figure 21:
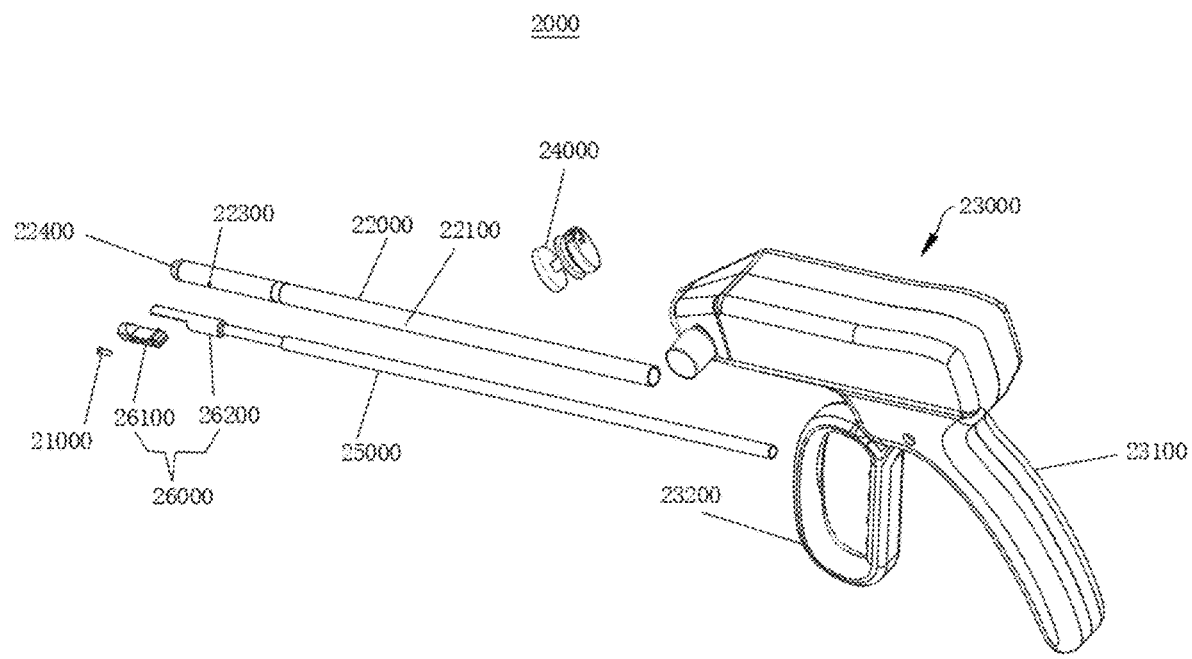
FIG. 21 is a schematic structural view illustrating a suture locker illustrated in FIG. 3.
Figure 22A:
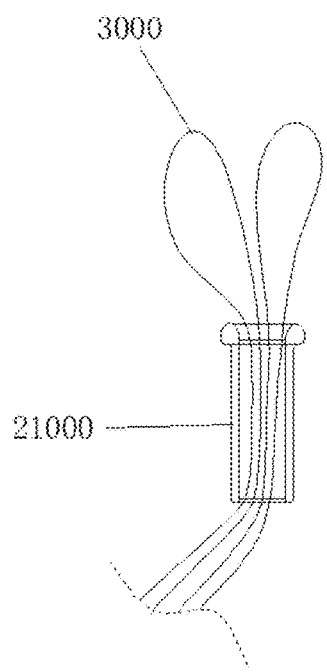
FIG. 22A is a schematic view illustrating that the suture is not fixed by a lock pin illustrated in FIG. 21.
Figure 22B:
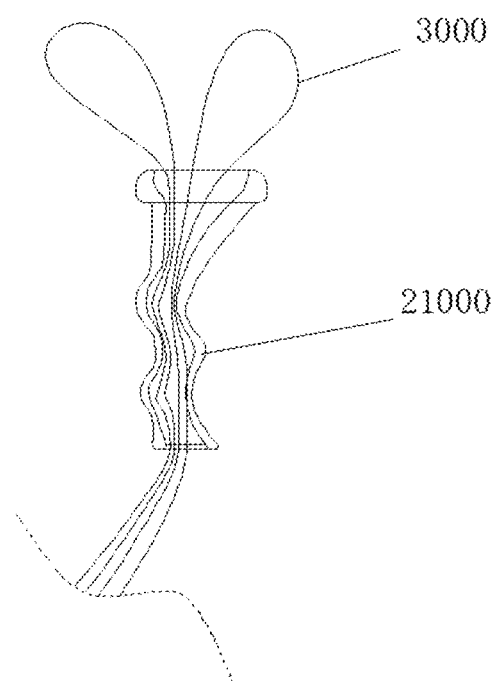
FIG. 22B is a schematic view illustrating that the suture is fixed by the lock pin illustrated in FIG. 21.
Figure 23A:
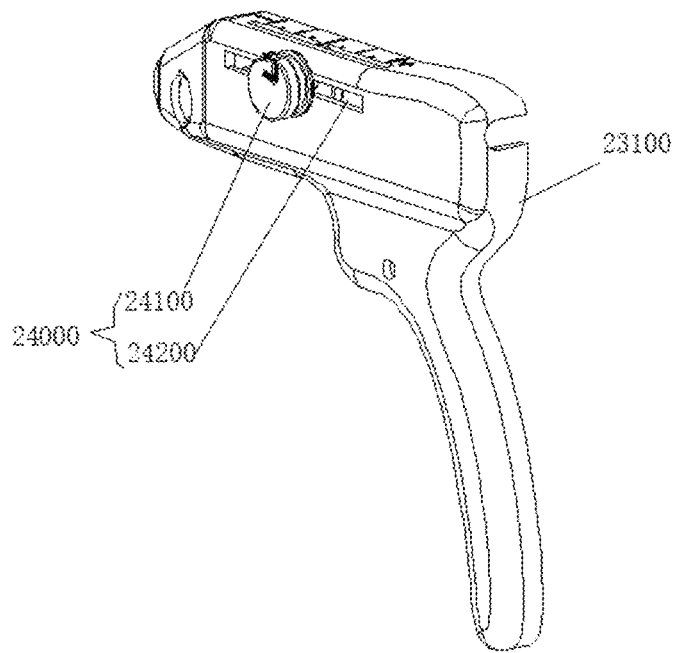
FIGS. 23A-23C are schematic structural views illustrating a handle of the suture locker illustrated in FIG. 21.
Figure 23B:
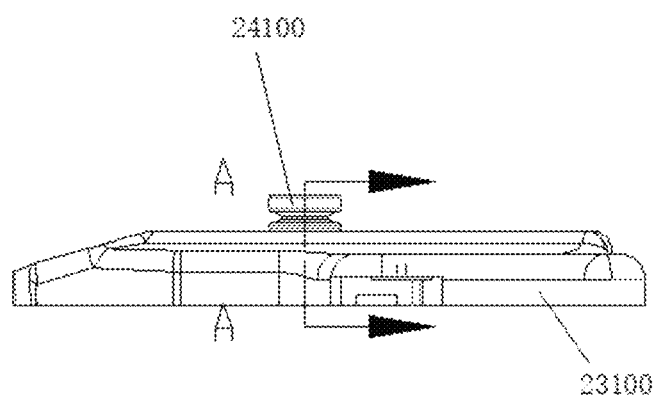
Figure 23C:
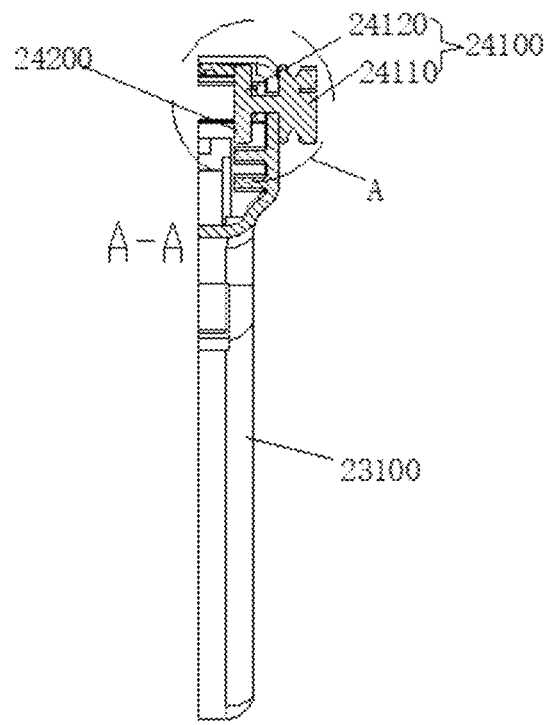
Figure 35A:
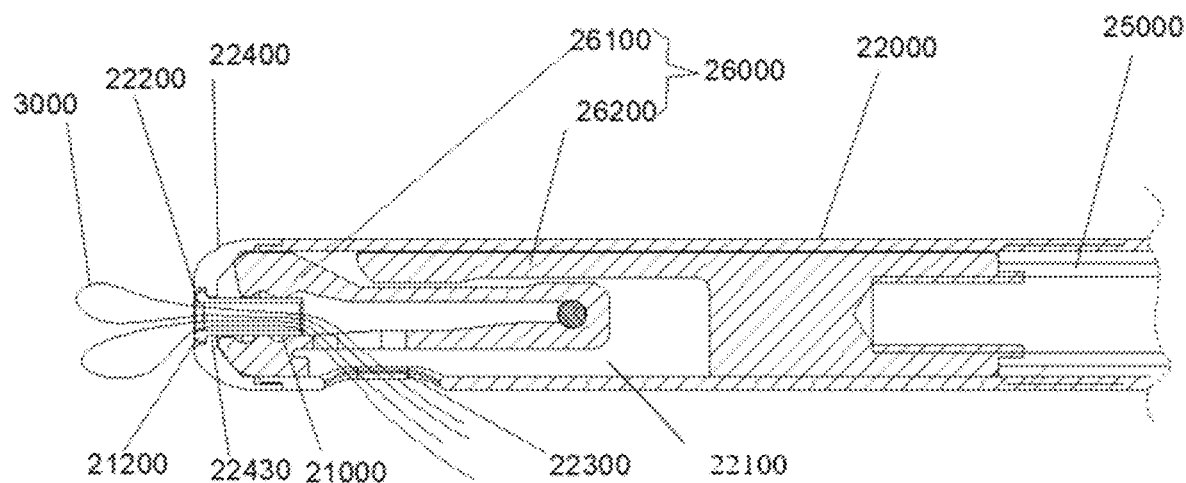
FIG. 35A is a schematic view illustrating that the lock pin is not squeezed by the suture locker illustrated in FIG. 21.
Figure 35B:
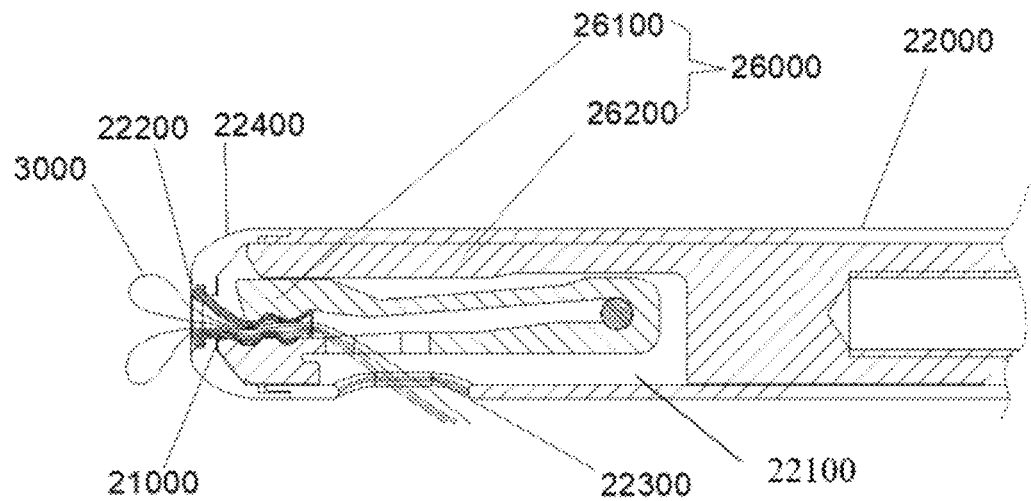
FIG. 35B is a schematic view illustrating that the lock pin is squeezed by the suture locker, where

As illustrated in FIG. 21, the suture locker 2000 includes a lock pin 21000, an outer shaft 22000, a handle 23000, and at least one adjusting device 24000. The lock pin 21000 is used to accommodate or fix the suture 3000 (referring to FIG. 22A or FIG. 22B, where FIG. 22A illustrates that the suture 3000 is not fixed by the lock pin 21000, and FIG. 22B illustrates that the suture 300 is fixed by the lock pin 21000). The outer shaft 22000 defines a receiving cavity 22100, and the lock pin 21000 is disposed at the distal end of the receiving cavity 22100 (as illustrated in FIGS. 35A-35B). The handle 23000 includes a fixing portion 23100 coupled to a proximal end of the outer shaft 22000. The adjusting device 24000 is disposed on the fixing portion 23100 (as illustrated in FIGS. 23A-23C). The adjusting device 24000 is coupled to the proximal end of the suture 3000 and used for adjusting tightening or loosening of the suture 3000. It can be understood that the adjusting device 24000 may be any device capable of adjusting the tightening or loosening of the suture 3000, such as a bunching device or a buckle. It can be understood that the number of the at least one adjusting device 24000 can be set according to need. Preferably, two adjusting devices 24000 are respectively disposed on two opposite sides of the fixing portion 23100 for adjusting two sets of sutures 3000 respectively.

With regard to the suture locker 2000 in this implementation, in the minimally invasive surgery or the interventional therapy, the adjusting device 24000 can be used to adjust, according to efficacy, the length of the suture 3000 in the process of fixing the suture 3000, thereby enhancing the surgical effect and improving the success rate of the surgery.

As illustrated in FIGS. 23A-23C, in a further implementation, the adjusting device 24000 includes a bunching device 24100 movably coupled to the fixing portion 23100. The bunching device 24100 is coupled to the proximal end of the suture 3000 to adjust the tightening or loosening of the suture 3000. By adjusting the tightening or loosening of the suture 3000 through the bunching device 24100, the length of the suture 3000 can be effectively controlled, and a slight adjustment of the length of the suture 3000 can be achieved. For example, the suture 3000 is wound on the bunching device 24100, and the suture 3000 is tightened or loosened by changing a winding direction or a winding manner.

In a further implementation, the adjusting device 24000 further includes an adjusting rail 24200 disposed on the fixing portion 23100. The bunching device 24100 is coupled to the fixing portion 23100 via the adjusting rail 24200. The bunching device 24100 can slide back and forward on the adjusting rail 24200 along an axial direction of the adjusting rail 24200, thereby adjusting the tightening or loosening of the suture 3000. It is to be understood that the bunching device 24100 adjusts the tightening or loosening of the suture 3000 when rolling along the adjusting rail 24200. It is to be understood that the axial direction of the adjusting rail 24200 coincides with the axial direction of the whole suture locker 2100, or the axial direction of the adjusting rail 24200 and the axial direction of the whole suture locker 2000 defines an angle of preset degrees to allow the bunching device 24100 to roll on the adjusting rail 24200, thereby adjusting the tightening or loosening of the suture 3000. The axial direction of the whole suture locker 2000 refers to a direction from the proximal end to the distal end.

Figure 26:
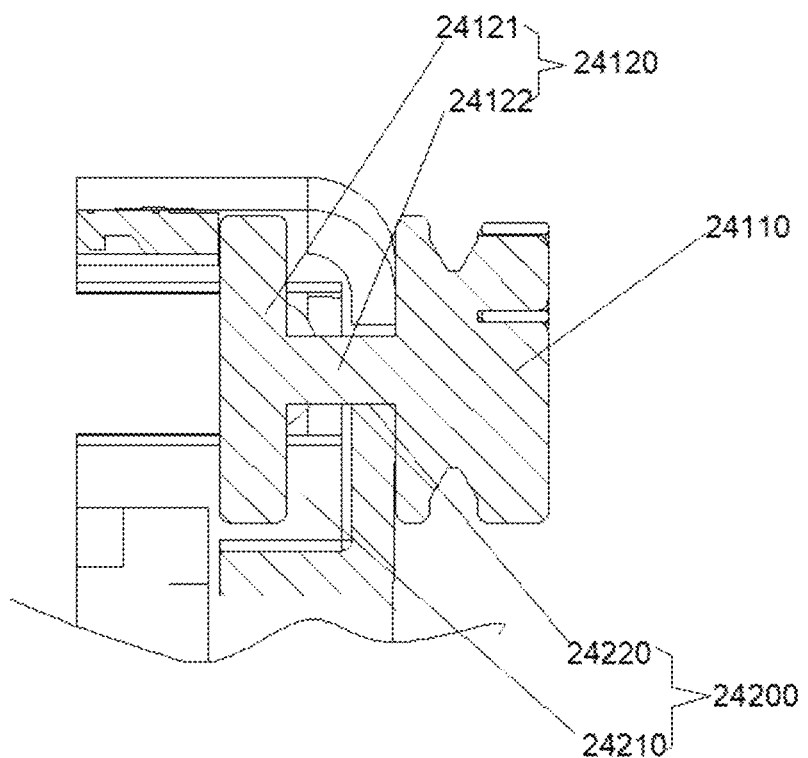
FIG. 26 is an enlarged view of a portion A of FIG. 23C.

As illustrated in FIGS. 24A-24B and FIGS. 23A-23C, in a further implementation, the bunching device 24100 includes a suture fixation 24110 and a handle connecting portion 24120 coupled with the suture fixation 24110. The suture fixation 24110 is detachably coupled to the suture 3000. The suture 3000 can be fixed to the suture fixation 24110 by winding, pressing, crimping, or the like. The handle connecting portion 24120 is disposed in the adjusting rail 24200 (as illustrated in FIG. 26). The bunching device 24100 can move back and forward on the adjusting rail 24200 along the axial direction of the adjusting rail 24200 via the handle connecting portion 24120. The handle connecting portion 24120 is disposed in the adjusting rail 24200 by snapping or the like to ensure that the bunching device 24100 cannot slip off the handle 3000.

Figure 24A:
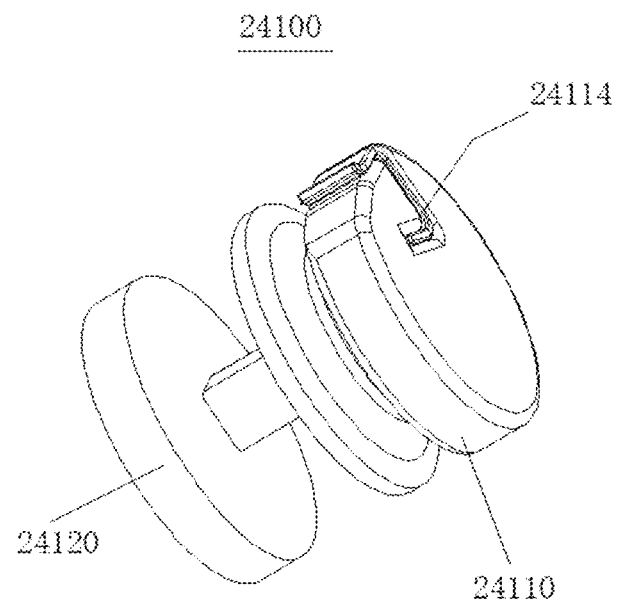
FIGS. 24A-24B are schematic structural views illustrating a bunching device of the suture locker illustrated in FIG. 21.
Figure 24B:
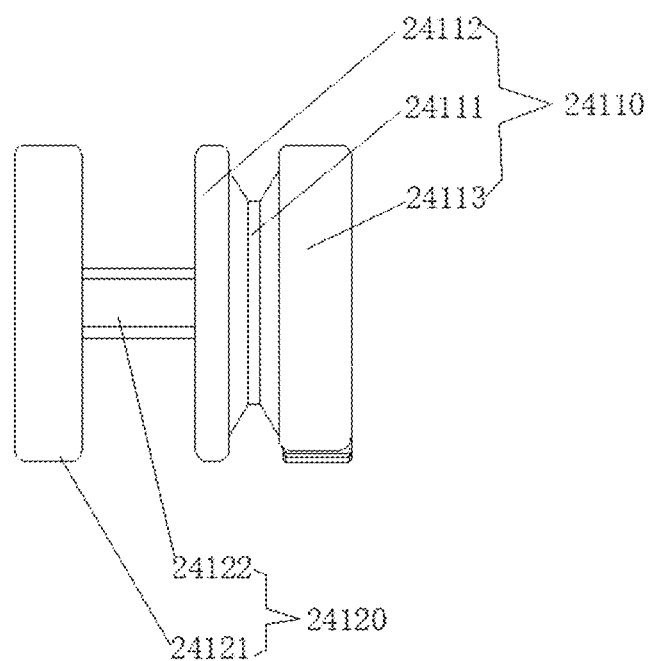

As illustrated in FIG. 24B, in a further implementation, the suture fixation 24110 includes a spool 24111, a first blocking portion 24112, and a second blocking portion 24113. The first blocking portion 24112 and the second blocking portion 24113 are respectively coupled to two opposite ends of the spool 24111. The second blocking portion 24113 is further away from the handle connecting portion 24120 than the first blocking portion 24112. When the suture 3000 is wound on the spool 24111, the first blocking portion 24112 and the second blocking portion 24113 at two ends of the spool 24111 can effectively prevent the suture 3000 from slipping off the spool 24111. It is to be understood that the first blocking portion 24112 and the second blocking portion 24113 each have a larger diameter than the spool 24111.

Figure 25:
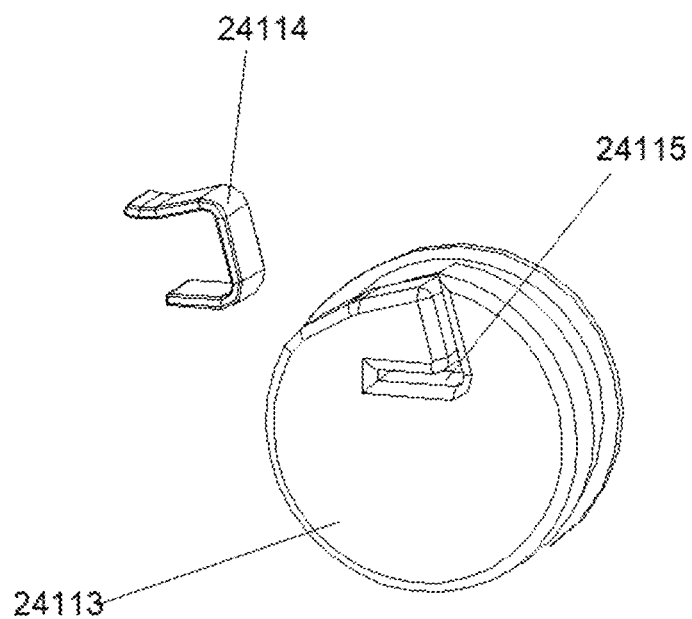
FIG. 25 is a schematic structural view illustrating a suture fixation of the bunching device of the suture locker illustrated in FIG. 21.

As illustrated in FIG. 24A, in a further implementation, the suture fixation 24110 further includes an elastic sheet 24114. The elastic sheet 24114 is fixed to the second blocking portion 24113. The elastic sheet 24114 is used to fix the suture 3000. As illustrated in FIG. 25, it is to be understood that the second blocking portion 24113 defines an elastic sheet receiving groove 24115. The elastic sheet 24114 is received in the elastic sheet receiving groove 24115. After the suture 3000 is wound on the spool 24111, the proximal end of the suture 3000 is fixed to the elastic sheet 24114 and received in the elastic sheet receiving groove 24115 to fix the proximal end of the suture 3000 to the bunching device 24100. It can be understood that the elastic sheet receiving groove 24115 may be designed to be in the shape of a corner, and the elastic sheet 24114 is designed to be adapted to the elastic sheet receiving groove 24115 having the shape of a corner. With setting of the shape of a corner, the suture 3000 cannot easily slip off the elastic sheet 24114 and is stably fixed.

As illustrated in FIGS. 23A-23C and FIG. 26, FIG. 26 is an enlarged view of a portion A illustrated in FIG. 23C. In a further implementation, the adjusting rail 24200 defines a rail cavity 24210 and has a rail outer wall 24220. The handle connecting portion 24120 includes an inserting portion 24121 and a connecting shaft 24122. The inserting end 24121 is disposed in the rail cavity 24120 and can move back and forward in the rail cavity 24210. The connecting shaft 24122 is disposed on the rail outer wall 24220 and can move back and forward on the rail outer wall 24220. The inserting portion 24121 is fixed to the suture fixation 24110 via the connecting shaft 24122. The inserting portion 24121 is disposed in the rail cavity 24210, and movement of the inserting portion 24121 is limited to be within the rail cavity 24120 due to the rail outer wall 24220, and thus the inserting portion 24121 cannot easily slip off the rail cavity 24210.

Figure 27A:
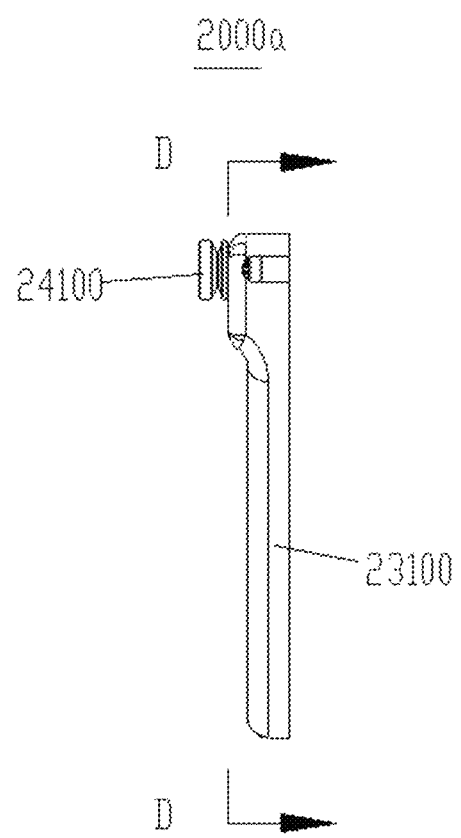
FIGS. 27A-27B are schematic structural views illustrating a handle of the suture locker according to another implementation, where
Figure 27B:
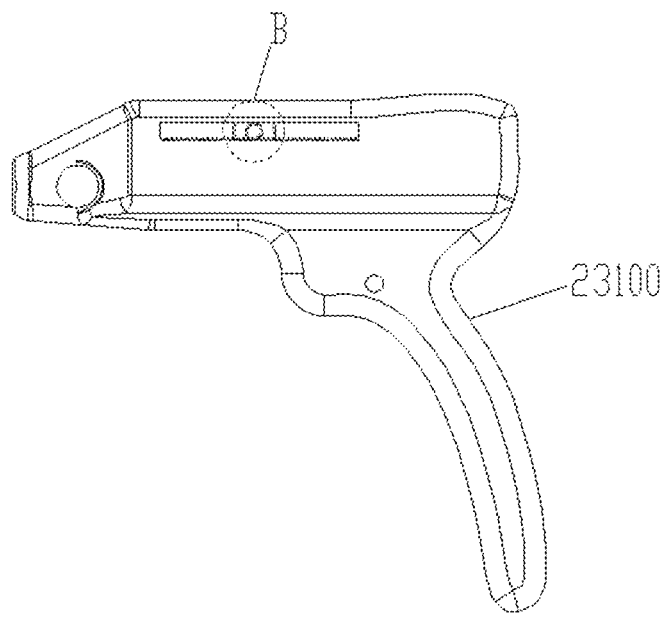
Figure 28:
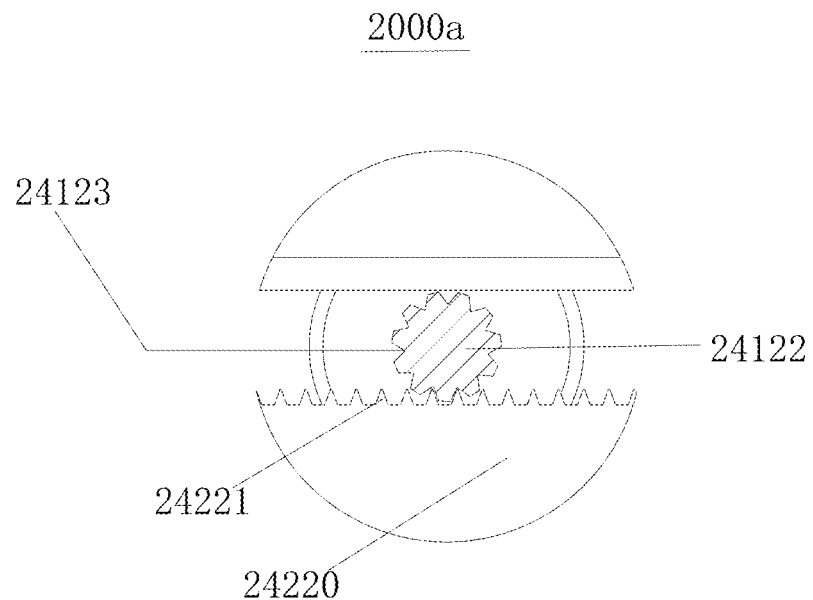
FIG. 28 is an enlarged view of a portion B of FIG. 27B.

As illustrated in FIGS. 27A-27B and FIG. 28, a suture locker 2000a according to another implementation is illustrated. FIG. 27A is a right view of the suture locker 2000a, where a handle of the suture locker 2000a is viewed. FIG. 27B is a cross-sectional view of the suture locker 2000a illustrated in FIG. 27A, taken along line D-D. FIG. 28 is an enlarged view of portion B of FIG. 27B. The suture locker 2000a differs from the suture locker 2000 in that the suture locker 2000a is provided with first teeth 24221 at the rail outer wall 24220 and second teeth 24123 at the connecting shaft 24122. The first teeth 24221 can be engaged with the second teeth 24123 to enable the connecting shaft 24122 to roll on the rail outer wall 24220, thereby driving the bunching device 24100 to move back and forward on the adjusting rail 24200 along the axial direction of the adjusting rail 24200. When the operator rotates the bunching device 24100, the bunching device 24100 moves along the axial direction of the adjusting rail 24200, and a rotational motion of the bunching device 24100 can be converted into a linear motion of the suture 3000, thereby accurately achieving the tightening and loosening of the suture 3000.

Figure 29:
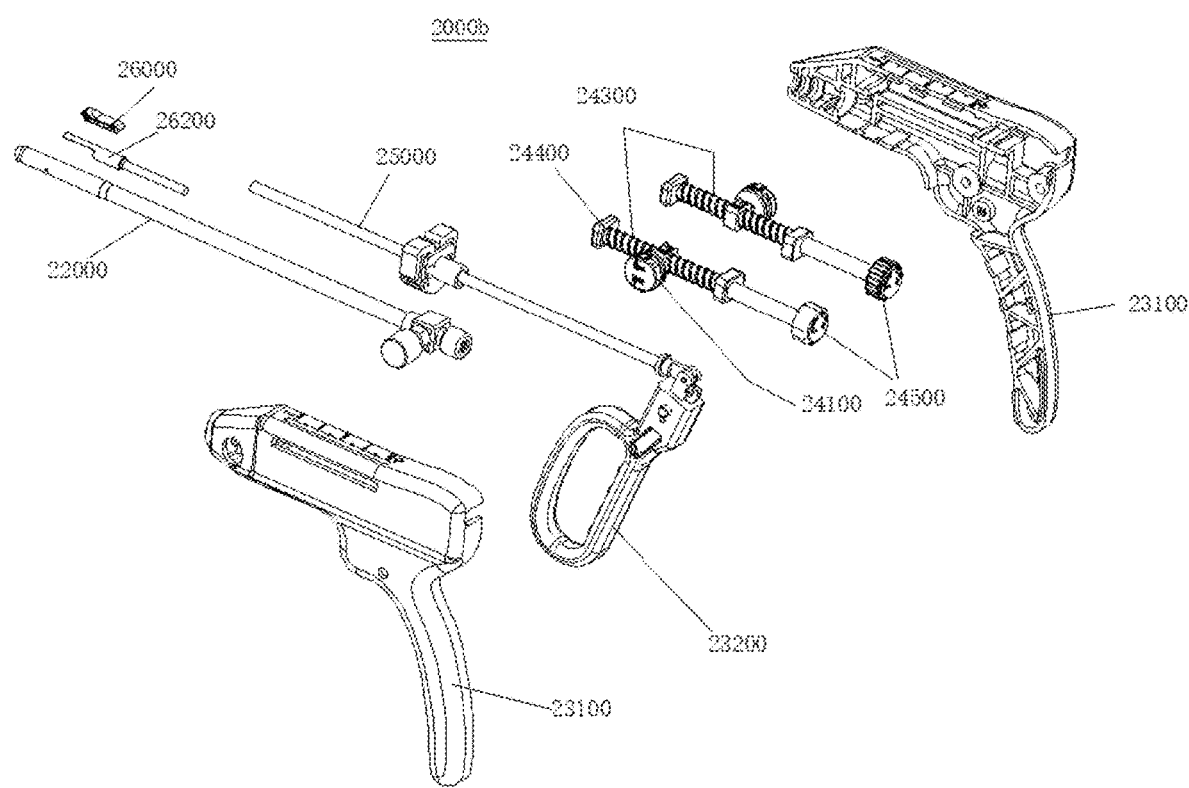
FIG. 29 is an exploded perspective view illustrating a handle of the suture locker according to another implementation.
Figure 30:
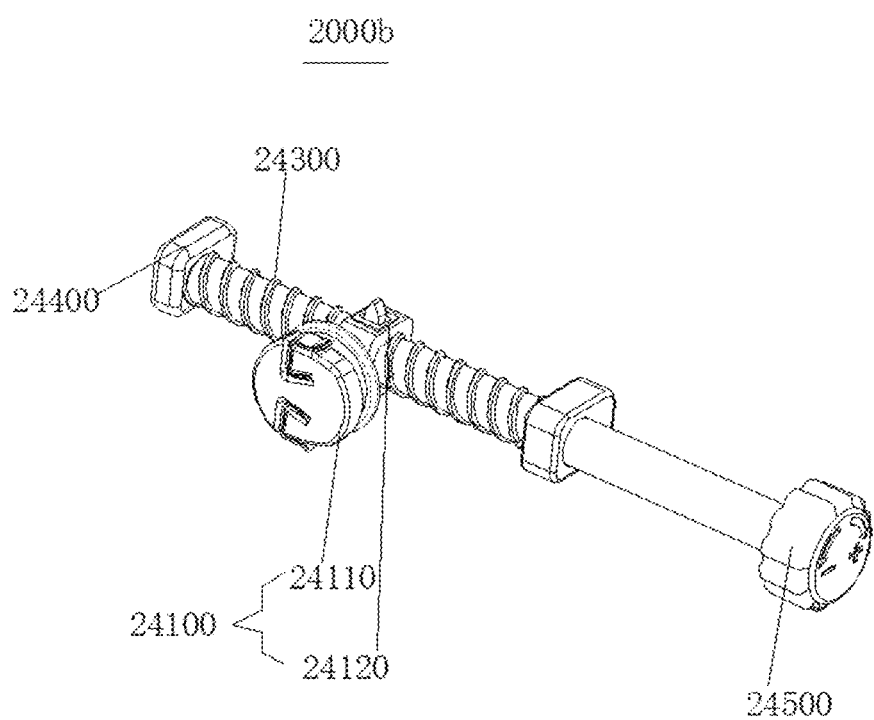
FIG. 30 is a schematic structural view illustrating an adjusting device of the suture locker illustrated in FIG. 29.

As illustrated in FIGS. 29-30, a suture locker 2000*b* according to another implementation is illustrated. The suture locker 2000*b* differs from the suture locker 2000 in that the adjusting device 24000 further includes lead screws 24300, bolts 24400, and adjusting knobs 24500. The lead screw 24300 is fixed in the fixing portion 23100 along the axial direction of the adjusting rail 24200. The bolt 24400 is fixed in the fixing portion 23100, and the lead screw 24300 passes through the bolt 24400 and is engaged with the bolt 24400. The proximal end of the lead screw 24300 passes through the proximal end of the fixing portion 23100 and is coupled to the adjusting knob 24500. The handle connecting portion 24120 is fixed to the lead screw 24300. The adjusting knob 24500 adjusts an axially forward or backward movement of the lead screw 24300. When the operator rotates the adjusting knob 24500, the adjusting knob 24500 drives the lead screw 24300 to rotate in the fixing portion 23100, thereby driving the bunching device 24100 coupled to the lead screw 24300 to move back and forward on the adjusting rail 24200 along the axial direction of the adjusting rail 24200.

Figure 31:
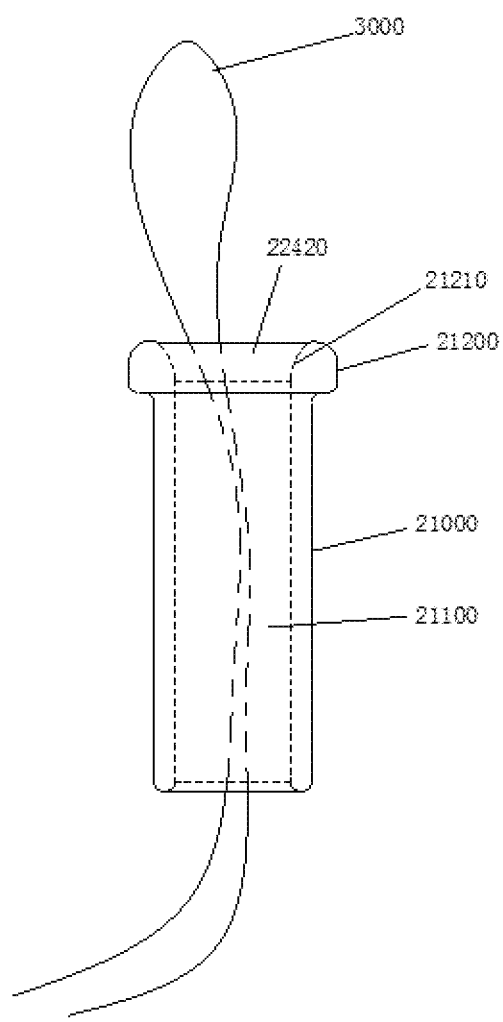
FIG. 31 is a perspective view illustrating the lock pin of the suture locker illustrated in FIG. 21.

Referring back to FIG. 21, in a further implementation, the handle 23000 further includes a movable portion 23200. The movable portion 23200 can move with respect to the fixing portion 23100. The lock pin 21000 defines a hollow inner cavity 21100 in the axial direction of the lock pin 21000 (as illustrated in FIG. 31). The hollow inner cavity 21100 is used to receive the suture 3000 and allow the suture 3000 to pass through. The suture locker 2000 further includes a squeezing assembly 26000 and a mandrel 25000. The squeezing assembly 26000 is to hold and press the lock pin 21000 to deform (refer to FIGS. 22A-22B, where FIG. 22A illustrates the lock pin un-deformed, and FIG. 22B illustrates the lock pin deformed). When the lock pin 21000 is subjected to a mechanical external force, the lock pin 21000 can be flattened to fix the suture 3000 in the deformed lock pin 21000, and no relative movement occurs between the suture 3000 and the lock pin 21000, thereby locking and fixing the suture 3000. The lock pin 21000 may be of various shapes, for example, may be in the shape of a cylinder, a prism, or the like, as long as the lock pin 21000 defines the hollow inner cavity 21100 for accommodating the suture 3000, the lock pin 21000 may be of any shape. In this implementation, the lock pin 21000 is in the shape of a cylinder to reduce a squeezing resistance.

Figure 34A:
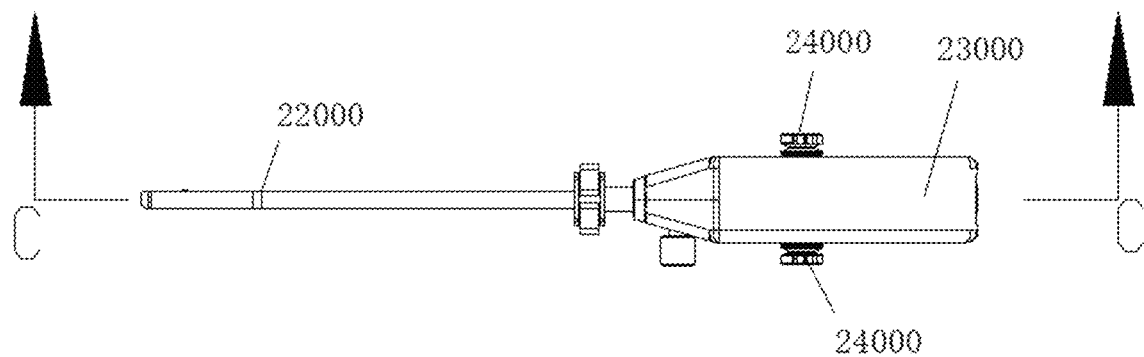
FIGS. 34A-34B are schematic views illustrating a process of squeezing the lock pin performed by the suture locker illustrated in FIG. 21.
Figure 34B:
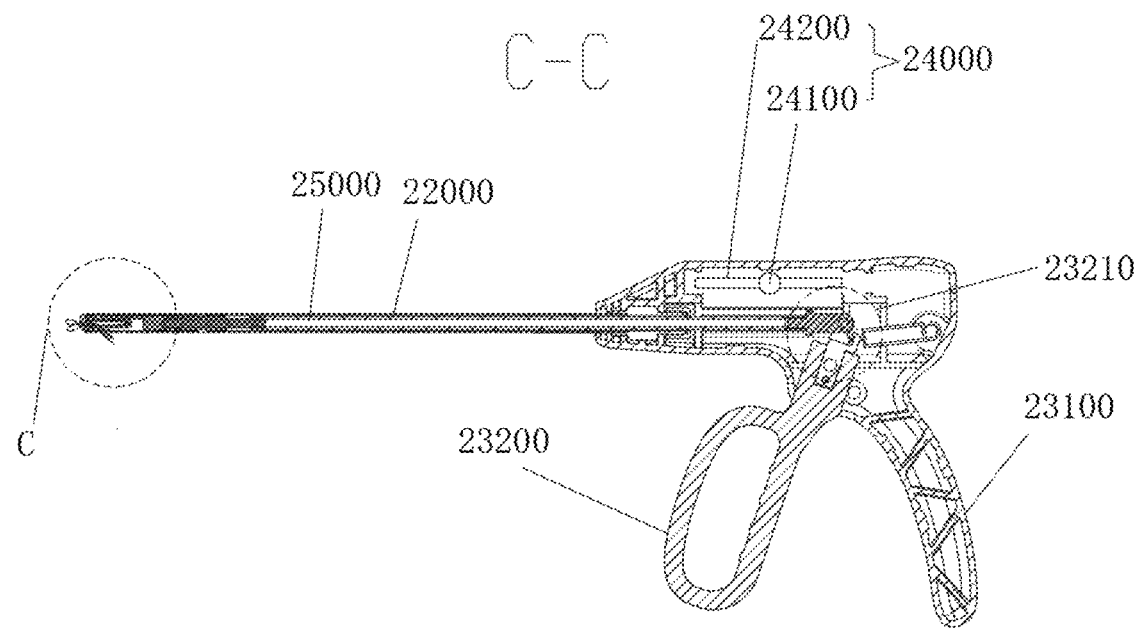

The distal end of the mandrel 25000 is coupled to the proximal end of the squeezing assembly 26000, and the proximal end of the mandrel 25000 is movably coupled to the movable portion 23200. The squeezing assembly 26000 and the mandrel 25000 are both received in the receiving cavity 22100, and the movable portion 23200 can move relative to the fixing portion 23100 to move the mandrel 25000, so as to cause the squeezing assembly 26000 to hold and press the lock pin 21000. It can be understood that the mandrel 25000 applies a force to the squeezing assembly 26000 during the movement of the mandrel 25000, so that the squeezing assembly 26000 can apply a mechanical external force to hold and press the lock pin 21000. The mandrel 25000 can extend to the fixing portion 23100, and a movable connecting portion 23210 between the movable portion 23200 and the mandrel 25000 is disposed in the fixing portion 23100 (as illustrated in FIGS. 34A-34B).

Figure 32:
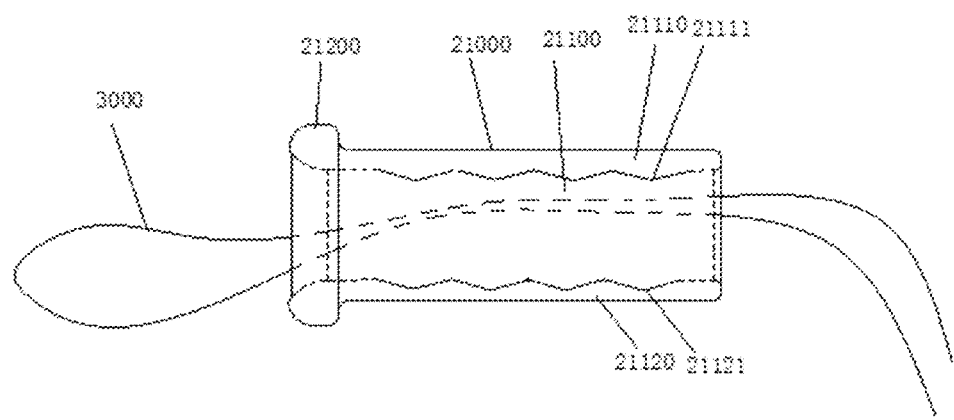
FIG. 32 is a perspective view illustrating a lock pin according to another implementation.

As illustrated in FIG. 32, in a further implementation, the hollow inner cavity 21100 of the lock pin 21000 has an upper surface 21110 and a lower surface 21120 opposite the upper surface 21110. A lock pad 21111 protrudes from the upper surface 21110, the lower surface 21120 defines a concave lock hole 21121, and the lock pad 21111 is adapted to the lock hole 21121. It can be understood that the upper surface and the lower surface are named when the lock pin 21000 is placed horizontally, and when the lock pin 21000 is placed vertically, the upper surface and the lower surface may also be called a left surface and a right surface. When the lock pin 21000 is deformed by an external squeezing force, the convex lock pad 21111 is pressed into the concave lock hole 21121. When the lock pin 21000 is further deformed, the lock pad 21111 and the lock hole 21121 are both deformed until the lock pad 21111 and the lock pin cannot be separated from each other. At this point, the suture 3000 is firmly fixed in the hollow inner cavity 21100 of the lock pin 21000.

Figure 33:
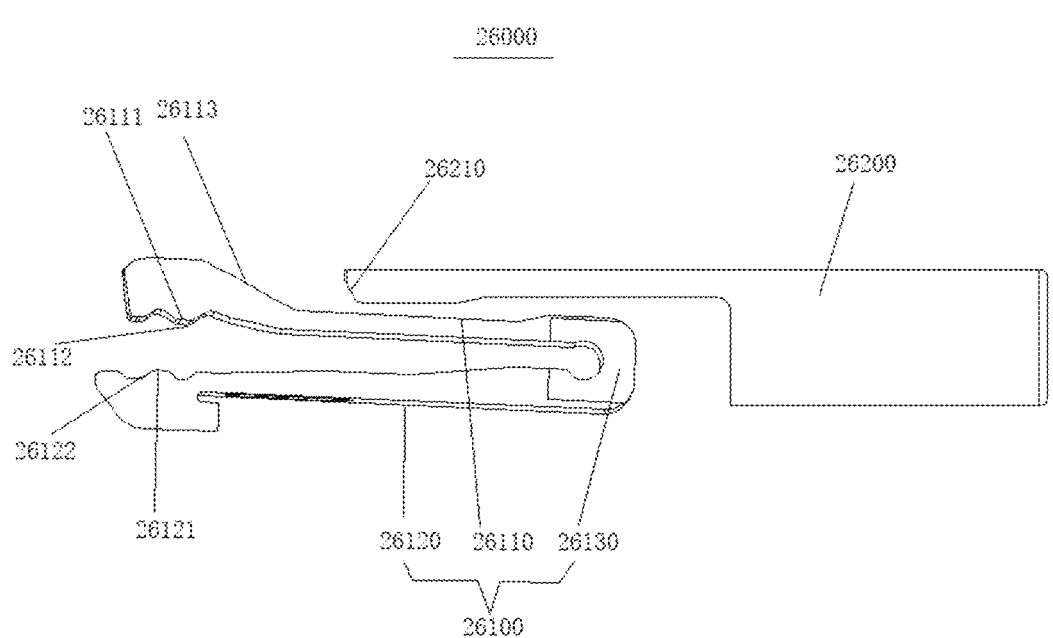
FIG. 33 is a schematic structural view illustrating a squeezing assembly of the suture locker illustrated in FIG. 21.

As illustrated in FIG. 33 and FIGS. 35A-35B, in a further implementation, the squeezing assembly 26000 includes a squeezing collet 26100 and a collet push rod 26200. The squeezing collet 26100 includes an upper clip 26110, a lower clip 26120, and a clip connecting portion 26130 coupled between a proximal end of the upper clip 26110 and a proximal end of the lower clip 26120. The lock pin 21000 is disposed between the upper clip 26110 and the lower clip 26120. A proximal end of the collet push rod 26200 is coupled to the distal end of the mandrel 25000. A distal end of the collet push rod 26200 is close to the upper clip 26110. The mandrel 25000 drives the collet push rod 26200 to move toward the upper clip 26110, thereby driving the upper clip 26110 to move toward the lower clip 26120 to make the upper clip 26110 and the lower clip 26120 cooperatively hold and press the lock pin 21000.

It is to be understood that, the upper clip 26110 and/or the lower clip 26120 are at least partially made from a deformable material and have certain elasticity. Therefore, when the upper clip 26110 and/or the lower clip 26120 is subjected to an external force, the deformable upper clip 26110 and the deformable lower clip 26120 may be driven to be close to each other, so as to hold and press the lock pin 21000 disposed between the upper clip 26110 and the lower clip 26120 to have a shape with a certain curvature. It can be understood that the upper clip 26110 and the lower clip 26120 are preferably made of stainless steel, nickel titanium alloy, cobalt chromium alloy or the like, and the clip connecting portion 26130 is made of stainless steel, nickel titanium alloy or the like. In this implementation, the whole squeezing collet 26100 is made of nickel-titanium alloy.

As illustrated in FIG. 33, in a further implementation, the upper clip 26110 has a first surface 26111 that faces the lock pin 21000, and the lower clip 26120 has a second surface 26121 that faces the lock pin 21000. A first engaging portion 26112 is formed on the first surface 26111, a second engaging portion 26122 is formed on the second surface 26121, and the first engaging portion 26112 can be engaged with the second engaging portion 26122 to enable the upper clip 26110 and the lower clip 26120 to be in a close state. It can be understood that the first engaging portion 26112 and the second engaging portion 26122 each may have a curvature shape or a sawtooth shape and can cooperate with each other.

When the lock pin 21000 is provided with a circular cone 21200 at the distal end thereof (see FIG. 32), the diameter of the circular cone 21200 is larger than that of the proximal end of the lock pin 21000. In order to cooperate with the lock pin 21000 with the circular cone 21200, in a further implementation, axial lengths of the upper clip 26110 and the lower clip 26120 are different. Preferably, a difference between the axial lengths of the upper clip 26110 and the lower clip 26120 equals a preset length. The preset length is at least equal to the thickness of the circular cone 21200. Thus, the circular cone 21200 of the lock pin 21000 non-pressed and the squeezing collet 26100 can be both placed at the distal end of the outer shaft 22000 without affecting a size of the outer shaft 22000. The thickness of the circular cone 21200 refers to the length of the circular cone 21200 along the axial direction of the lock pin 21000.

In a further implementation, the distal end of the collet push rod 26200 has a first inclined surface 26210, and the first inclined surface 26210 is inclined downwardly along a direction from the distal end to the proximal end. The upper clip 26110 has a second inclined surface 26113 that faces away from the lock pin 21000, and the second inclined surface 26113 is inclined downwardly along a direction from the distal end to the proximal end to ensure that there is a relatively large contact area between the squeezing collet 26100 and the collet push rod 26200. Preferably, a slope of the first inclined surface 26210 is smaller than that of the second inclined surface 26113. The slope of the first inclined surface 26210 refers to an included angle defined between the first inclined surface 26210 and a direction from the distal end of the collet push rod 26200 to the proximal end of the collet push rod 26200, and the slope of the second inclined surface 26113 refers to an included angle defined between the second inclined surface 26113 and a direction from the distal end of the collet push rod 26200 to the proximal end of the collet push rod 26200, and thus during that the collet push rod 26200 moves toward the distal end, the first inclined surface 26210 at the distal end of the collet push rod 26200 can continuously squeeze the second inclined surface 26113 of the upper clip 26110, so that the upper clip 26110 gradually gets close to the lower clip 26120, thereby continuously deforming the lock pin 21000 until the lock pin 21000 can no longer be deformed. At this point, the lock pin 21000 and the suture 3000 are firmly fixed together. The collet push rod 26200 is made of stainless steel, nickel-titanium alloy or cobalt-chromium alloy, and is preferably made of stainless steel.

It can be understood that the distal end of the collet push rod 26200 and the proximal end of the collet push rod 26200 form an L-shaped structure, that is, a radial thickness of the distal end of the collet push rod 26200 is smaller than that of the proximal end of the collet push rod 26200, and the distal end of the collet push rod 26200 is at one side of the whole collet push rod 26200, such that the distal end of the collet push rod 26200 and the proximal end of the collet push rod 26200 form the L-shaped structure. When the collet push rod 26200 is advanced to hold and press the squeezing collet 26100 downwardly, the L-shaped collet push rod 26200 enables the squeezing collet 26100 in the pressed state to be disposed in the L-shaped structure, such that a difference between a thickness of the whole structure formed by the collet push rod 26200 and the squeezing collet 26100 pressed and a thickness of the squeezing collet 26100 non-pressed is relatively small, thereby not affecting the size of the outer shaft 22000.

It can be understood that the collet push rod 26200 may be a hollow tube or have a solid rod-like structure.

Referring to FIGS. 34A-34B and FIGS. 35A-35B, FIG. 35A is a schematic view illustrating that the suture locker does not hold and press the lock pin, FIG. 35B is a schematic view illustrating that the suture locker holds and presses the lock pin, and FIG. 35A is an enlarged view of a portion C of FIG. 34B. In a further implementation, the distal end of the outer shaft 22000 defines a suture inlet 22200 along the radial direction of the outer shaft 22000. A diameter of the suture inlet 22200 is at least equal to the diameter of a portion of the lock pin 21000, where the portion of the lock pin 21000 has a maximum outer diameter, and thus the lock pin 21000 pressed can slip off the distal end of the outer shaft 22000. The outer shaft 22000 further defines a suture outlet 22300. The suture inlet 22200 and the suture outlet 22300 communicate with the hollow inner cavity 21100 of the lock pin 21000, respectively, so that the proximal end of the suture 3000 can sequentially pass through the suture inlet 22200, the proximal end of the lock pin 21000, and the suture outlet 22300. It can be understood that, in other implementations, the suture outlet 22300 may be in any position of the outer shaft 22000 or in the handle 23000, as long as the suture outlet 22300 communicates with the hollow inner cavity 21100 of the lock pin 21000, i.e., the proximal end of the suture 3000 can pass through the suture outlet 22300.

In a further implementation, the outer shaft 22000 is provided with a holding portion 22400 at the distal end thereof, and the diameter of the holding portion 22400 gradually decreases from the proximal end to the distal end. The holding portion 22400 is used to prevent the lock pin 21000 non-pressed from slipping off the distal end of the outer shaft 22000. The diameter of the holding portion 22400 gradually reduces from the proximal end to the distal end, thereby facilitating driving the distal end of the outer shaft 22000 to enter the patient's body and smoothly move in the body.

Figure 36A:
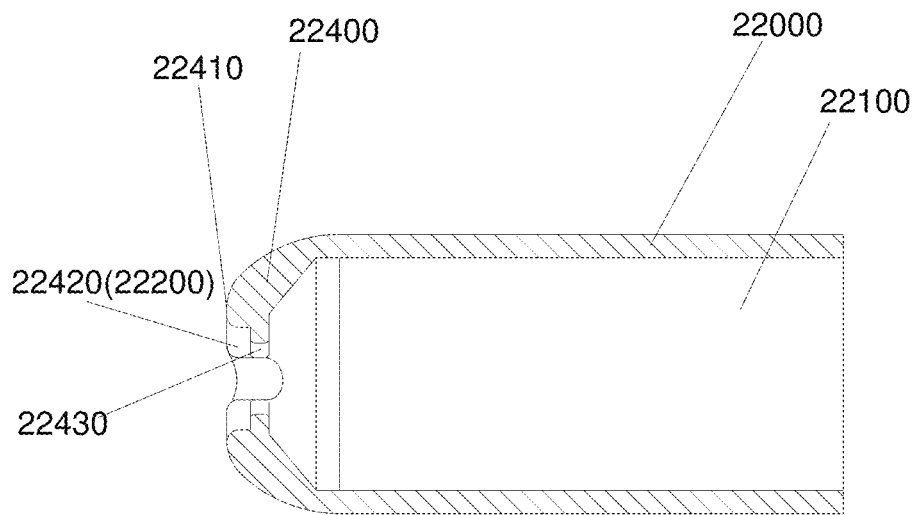
FIGS. 36A-36B are schematic structural views illustrating a holding portion of the suture locker illustrated in FIG. 21.
Figure 36B:
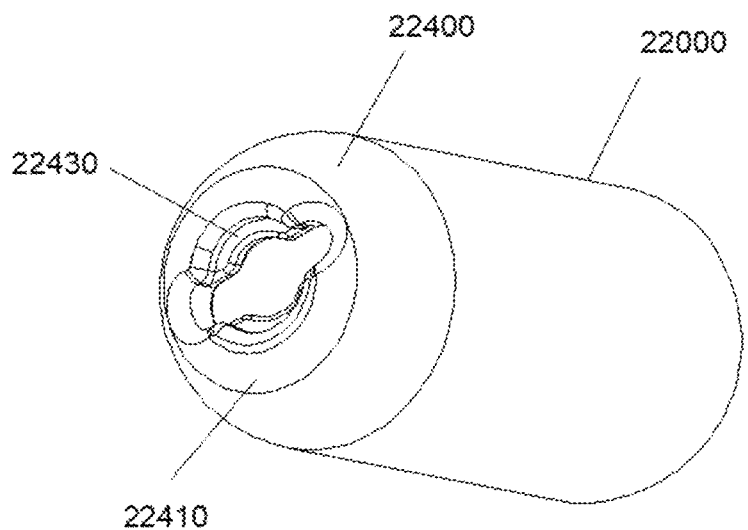

As illustrated in FIGS. 36A and 36B, in a further embodiment, the holding portion 22400 has a holding portion end face 22410 at the distal end thereof. The holding portion 22400 defines a holding portion opening 22420 penetrating the holding portion end face 22410 in the axial direction of the holding portion 22400, and the holding portion opening 22420 communicates with the receiving cavity 22100. The holding portion opening 22420 is the suture inlet 22200.

In a further implementation, a protrusion 22430 is formed at the holding portion opening 22420 in a radial direction of the holding portion opening 22420 (see FIG. 35A). A preset distance exists between the protrusion 22430 and the holding portion end surface 22410. The lock pin 21000 is partially disposed in the holding portion opening 22420, so that the protrusion 22430 can fix the lock pin 21000.

As illustrated in FIG. 36A, FIG. 36B, FIG. 35A, FIG. 35B, and FIG. 31, in a further implementation, the lock pin 21000 is provided with the circular cone 21200 at the distal end thereof. The diameter of the circular cone 21200 is larger than that of the proximal end of the lock pin 21000, and the circular cone 21200 is formed in the holding portion opening 22420. The protrusion 22430 fixes the lock pin 21000, thereby preventing the lock pin 21000 from slipping off the distal end of the outer shaft 22000. With the circular cone 21200, the transition between the hollow inner cavity 21100 of the lock pin 21000 and the distal end of the lock pin 21000 is enabled to be smooth to the greatest extent, thereby preventing a connection portion between the hollow inner cavity 21100 and the distal end of the lock pin 21000 from cutting off the suture 3000 or scratching internal tissues of the patient's body. It can be understood that the preset distance is at least equal to the thickness of the circular cone 21200, so that the circular cone 21200 is arranged between the protrusion 22430 and the holding portion end surface 22410, thereby facilitating stability of the lock pin 21000.

As illustrated in FIG. 31, in a further implementation, the circular cone 21200 has an arc-shaped inner sidewall 21210, such that the suture 3000 can smoothly pass through the lock pin 21000, thereby preventing the lock pin 21000 from cutting off the suture 3000 or damaging human tissues.

In a further implementation, the outer shaft 22000 and the mandrel 25000 may both be manufactured by processing a metal material such as stainless steel, nickel titanium, pure titanium or the like, or can be manufactured by processing a polymer material such as acrylonitrile butadiene styrene (ABS), polystyrene (PS), polyether ether copper (PEEK), or the like. The outer shaft 22000 and the mandrel 25000 may be made from the same material or different materials. The outer shaft 22000 and the mandrel 25000 may be preferably made of stainless steel.

In a further implementation, the lock pin 21000 is made of stainless steel, pure titanium, nickel titanium, cobalt chromium alloy, or the like, and preferably made of pure titanium or stainless steel.

When using the suture locker 2000, the operator first enables the proximal end of the suture 3000 to sequentially pass through the suture inlet 22200 on the distal end of the outer shaft 22000, the opening on the distal end of the lock pin 21000, and the suture outlet 22300 on the distal end of the outer shaft 22000, and then enables the suture 3000 to be fixed to the suture fixation 24110 of the bunching device 24100. The length of the suture 3000 is adjusted by the adjusting device 24000 according to need. After adjustment, the movable portion 23200 of the handle 23000 is driven to move toward the fixing portion 23100, thereby driving the mandrel 25000 to move toward the distal end with respect to the outer shaft 22000, thereby causing the collet push rod 26200 to hold and press the squeezing collet 26100. The upper clip 26110 and the lower clip 26120 of the squeezing collet 26100 hold and press the lock pin 21000 to deform the lock pin 21000 (Refer to FIG. 35A, where FIG. 35A illustrates the lock pin 21000 non-pressed, and FIG. 35B illustrates the lock pin 21000 pressed), and then the suture 3000 received in the lock pin 21000 is fixed in the lock pin 21000.

The following illustrates an implementation process of repairing and treating the mitral regurgitation by the adjustable heart valve repair system provided in the implementation.

Figure 37:
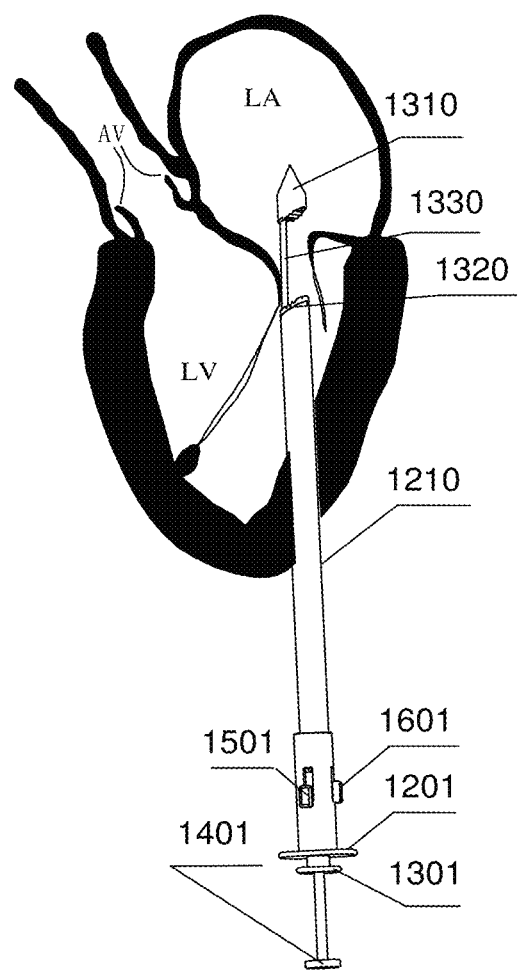
FIGS. 37-49 are schematic structural views illustrating a process of repairing leaflets of a mitral valve by an adjustable heart valve repair system according to the present disclosure.

Referring to FIG. 37, at S1, the distal end of the suture implanting apparatus 1000 is pushed into a left ventricle through the apex of the heart until the distal clamp 1310 and the proximal clamp 1320 are both disposed in the left atrium.

Figure 38:
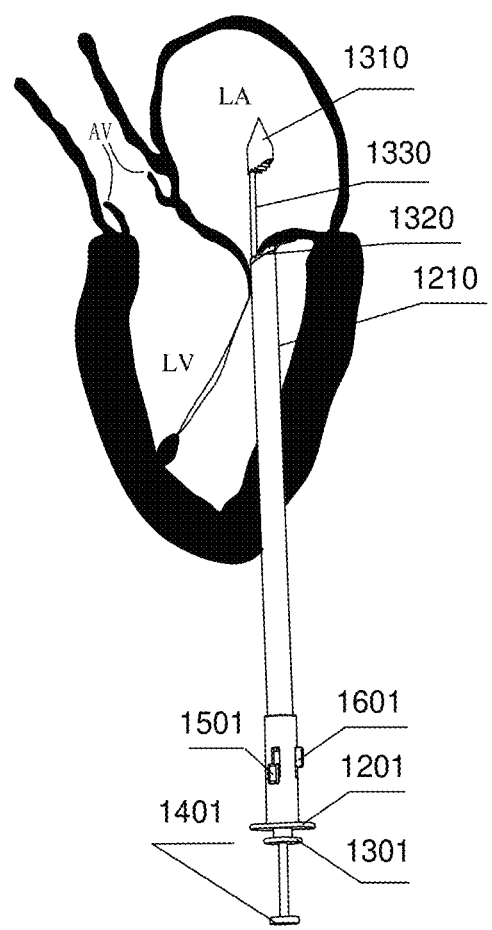

Referring to FIG. 38, at S2, the pushing shaft 1210 is drawn back toward the proximal end or the clamping push rod 1330 is pushed toward the distal end, so that the proximal clamp 1320 is separated from the distal clamp 1310. The fourth handle 1501 is pushed toward the distal end to drive the clamping auxiliary arm 1520 to push the clamping auxiliary member 1510 out of the opening 1260. At this point, the clamping auxiliary member 1510 locates below the lower surface of the leaflet to assist in stabilizing the pulsatile leaflet (see FIG. 13B). A relative position among the first handle 1201, the second handle 1301, and the fourth handle 1501 remains unchanged, and the entire instrument is moved slowly toward the proximal end until the leaflet enters the leaflet receiving space defined between the proximal clamp 1320 and the distal clamp 1310. The clamping auxiliary member 1510 can provide the leaflet with a certain support.

Figure 39:
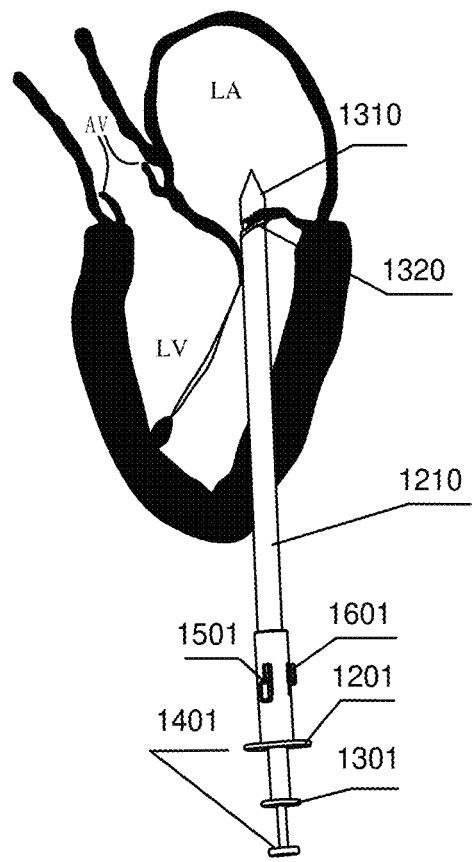

Referring to FIG. 39, at S3, the distal end of the suture implanting apparatus 1000 is slightly moved until the edge of the leaflet is in contact with the clamping push rod 1330. At this point, the second handle 1301 is drawn back toward the proximal end to drive the distal clamp 1310 to move toward the proximal clamp 1320 until the distal clamp 1310 and the proximal clamp 1320 are in the close state, thereby clamping the leaflet.

At S4, the position of the first handle 1201 is kept unchanged, and the detecting handle 1601 is pushed toward the distal end to drive the probe 1610 to move toward the distal end along the axial direction of the pushing shaft 1210. If the leaflet is poorly clamped, that is, the leaflet does not fully cover the probe opening 1321 on the clamping surface of the proximal clamp 1320, the distal end of the probe 1610 can extend out of the probe opening 1321 and enter the probe receiving cavity 1312 of the distal clamp 1310. The operations at S2 and S3 need to be repeated to re-clamp the leaflet. If the leaflet is well clamped, that is, the leaflet completely covers the probe opening 1321 on the clamping surface of the proximal clamp 1320, the distal end of the probe 1610 cannot extend out of the probe opening 1321 and cannot enter the probe receiving cavity 1312 of the distal clamp 1310, and thus subsequent operations can be performed. If the operator finds that the leaflet is not effectively clamped, the relative position between the distal clamp 1310 and the proximal clamp 1320 can be slightly adjusted to make that there is a certain distance between the distal clamp 1310 and the proximal clamp 1320. The relative position between the clamping push rod 1330 and the leaflet is then adjusted. The clamping assembly 1300 is operated again to clamp the leaflet, and then the surgical operation at the S5 is performed. During adjusting, since the clamping auxiliary assembly 1500 locating below the leaflet can support the leaflet, the leaflet can be prevented from slipping off the clamping assembly 1300.

Figure 40:
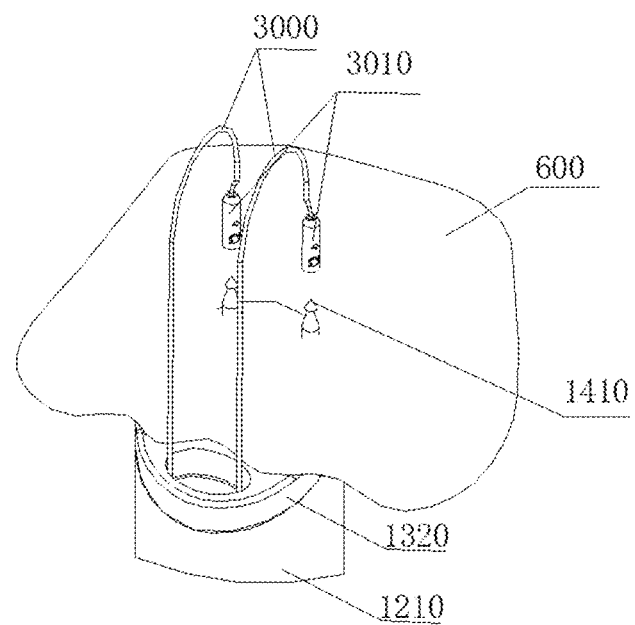
Figure 41:
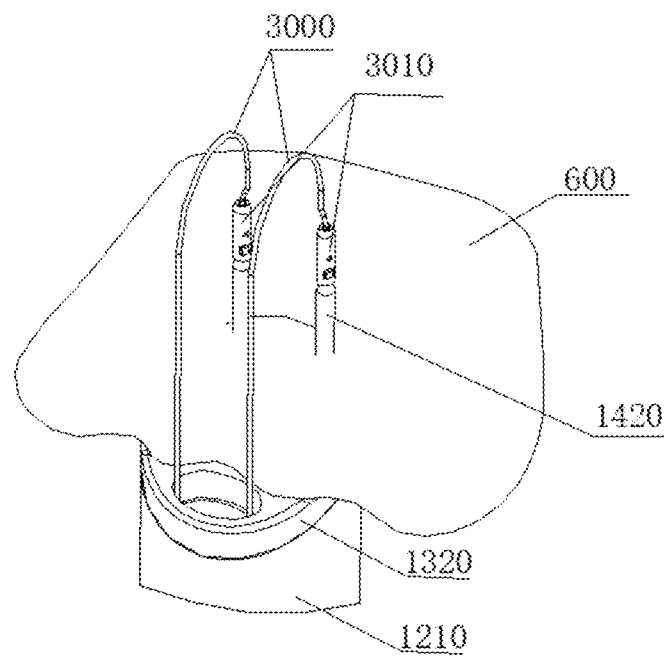

Referring to FIG. 40 and FIG. 41, at S5, the third handle 1401 is pushed toward the distal end to drive the puncturing needle 1410 to move toward the distal end, until the puncturing needle 1410 punctures the leaflet and is fixedly coupled to the fixing member 3010 of the suture 3000.

Figure 42:
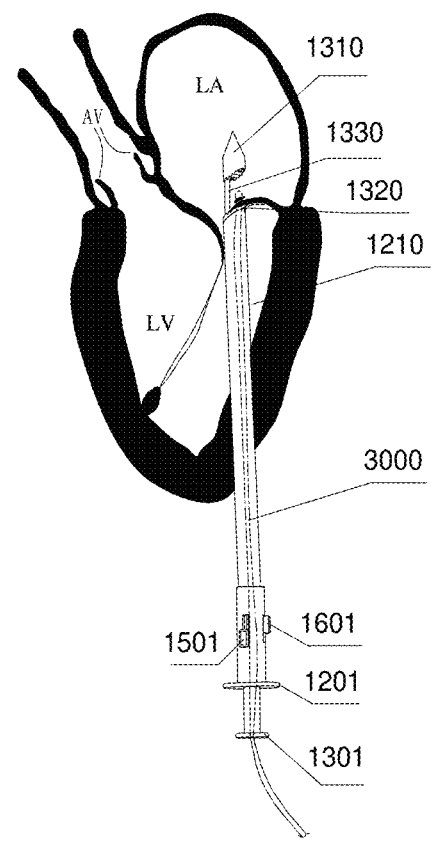
Figure 43:
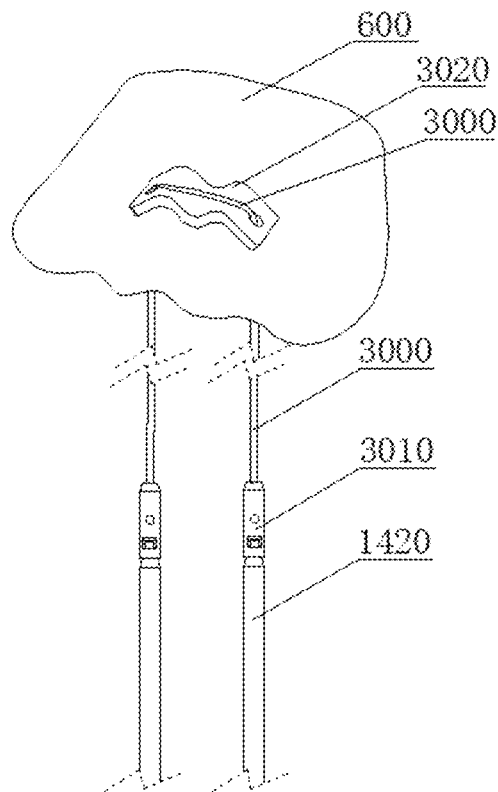

Referring to FIG. 42 and FIG. 43, at S6, the third handle 1401 is drawn back, such that the puncturing needle 1410 drives the fixing member 3010 of the suture 3000 and the suture 3000 coupled to the fixing member 3010 to pass through the leaflet sequentially, and the anti-slip member 1130 is pulled out of the clamping surface of the distal clamp 1310. A contact surface (i.e., lower surface) of the anti-slip member 1130 is in contact with the upper surface of the leaflet, and part of the suture 3000 presses an upper surface of the anti-slip member 1130 to enable the anti-slip member 1130 to abut against the leaflet. At this point, a point contact between the suture 3000 and the leaflet is changed to be a surface contact between the anti-slip member 1130 and the leaflet, thereby effectively reducing a risk of tearing of the leaflet.

At S7, the third handle 1401 is further drawn back until the fixing member 3010 is drawn back from the proximal end of the pushing shaft 1210, and then the fourth handle 1501 is drawn back to drive the clamping auxiliary member 1510 to be drawn back into the auxiliary arm receiving cavity 1250, and then the whole suture implanting apparatus 1000 is drawn back to complete suture implantation for one leaflet of the mitral valve.

Figure 44:
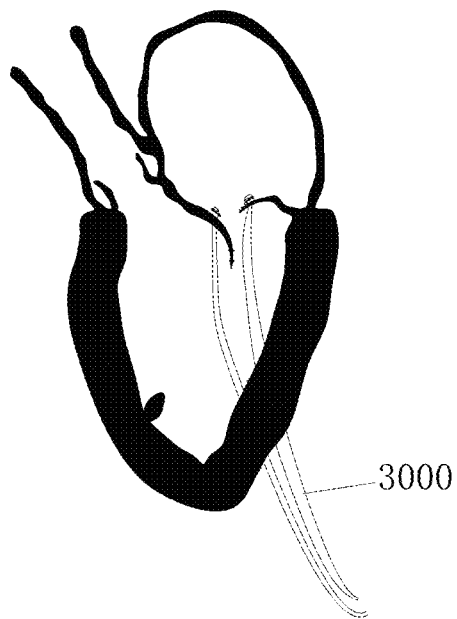
Figure 45:
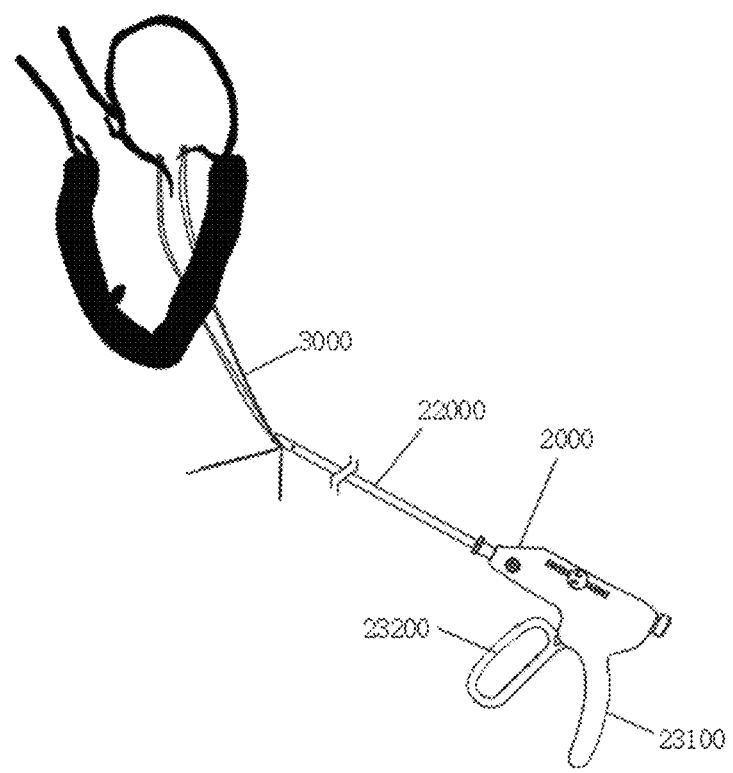

At S8, the operations from S1 to S7 are repeated to complete the suture implantation for the other leaflet of the mitral valve (see FIG. 44). Outside the patient's body, the multiple sutures 3000 in both the leaflets are all inserted into the lock pin 21000 of the suture locker 2000b, and the proximal ends of the sutures 3000 are enabled to pass through the suture outlet 22300 on the distal body of the outer shaft 22000 (see FIG. 45). The sutures in the anterior leaflet and posterior leaflet are distinguished, and the proximal ends of the two sets of sutures 3000 are respectively wound on the spools of the bunching devices 24100, and then the proximal ends of the sutures 3000 are fixed to the elastic sheets 24114 to maintain the relative position between the sutures 3000 and the locking pin 21000.

Figure 46:
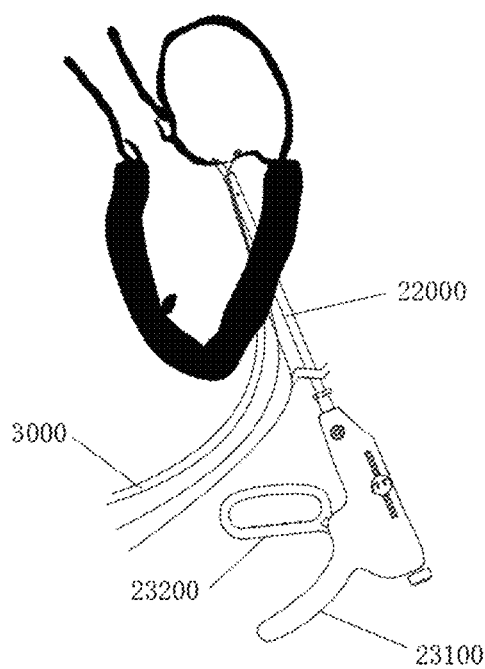
Figure 47:
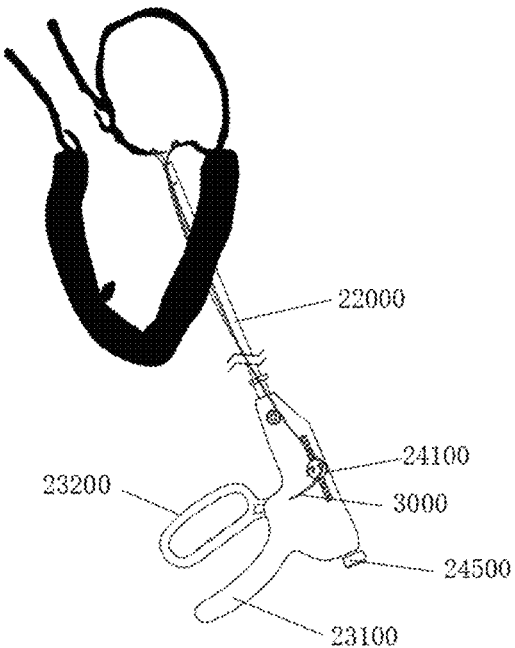

At S9, the distal end of the suture locker 2000b is pushed into the heart through the apex of the heart and is moved to be close to the leaflet of the mitral valve to pull the suture 3000, until the distal end of the suture locker 2000b reaches a predetermined position that is below the leaflet. It can be understood that at S8 and S9, after the suture 3000 passes through the suture outlet 22300, the distal end of the suture locker 2000b is first pushed into the heart through the apex of the heart and then is moved to be close to the leaflet of the mitral valve (see FIG. 46), and then the suture 3000 is fixed to the elastic sheet 24114.

At S10, the two adjusting knobs 24500 are rotated respectively to drive the two lead screws 24300 to rotate, thereby driving each bunching device 24100 connected to one lead screw 24300 to move back and forward in the adjusting rail along the axis direction of the adjusting rail 24200, so as to adjust the tightness of the two set of sutures 3000 coupled to the bunching devices 24100 respectively, and determine, by ultrasound, a state in which the mitral regurgitation is slightest. When the state reaches, the rotation of the adjusting knobs 24500 are stopped to maintain the tightness of the two set of sutures 3000, that is, to maintain a relative distance between the anterior leaflet and the posterior leaflet.

At S11, as illustrated in FIG. 34A, FIG. 34B, FIG. 35A, FIG. 35B, and FIG. 47, the fixing portion 23100 of the handle 23000 remains unchanged, and the movable portion 23200 is driven to move toward the fixing portion 23100 until the movable portion 23200 cannot be further moved. At this point, the mandrel 25000 and the collet push rod 26200 move toward the distal end with respect to the outer shaft 22000. The distal end of the collet push rod 26200 continuously squeezes the collet 26100, so that the upper clip 26110 and the lower clip 26120 of the collet 26100 get close to each other to hold and press the lock pin 21000 between the upper clip 26110 and the lower clip 26120, until the lock pin 21000 is deformed and the sutures 3000 in the lock pin 21000 are fixed together. The deformed lock pin 21000 slips off the suture inlet 22200 on the distal end of the outer shaft 22000 of the suture locker 2000b.

Figure 48:
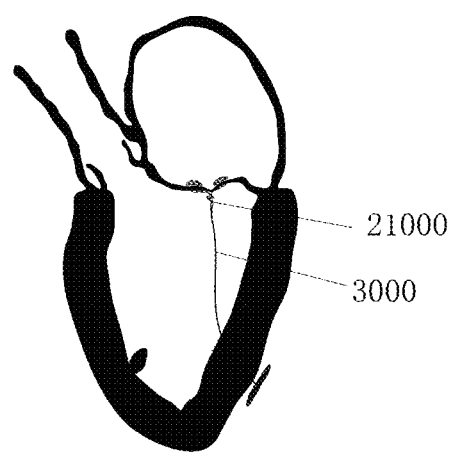
Figure 49:
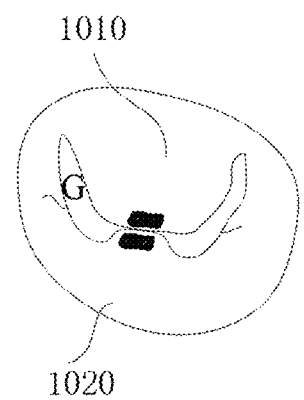

At S12, the distal end of the suture locker 2000b is pulled out of the patient's body, the lock pin 21000 stays in the patient's body, and the proximal end of the suture 3000 is fixed to the apex of the heart or the papillary muscle. At this point, with the lock pin 21000, the two sets of sutures 3000 in the anterior leaflet and the posterior leaflet are fixed together (see FIG. 48), and the edge-to-edge repair for the mitral valve is completed, thereby forming a double-orifice structure (see FIG. 49). It can be understood that in this step, the operator does not need to fix the proximal end of the suture 3000 to the apex of the heart or the papillary muscle, and what is needed is to snip the proximal end of the suture 3000.

It can be understood that after the operation at S7, the operator fixes the distal end of the suture 3000 to the apex of the heart, the papillary muscle, or the ventricular wall, that is, the suture 3000 can be used as an artificial chordae tendineae to complete the "chordae tendineae repair" of the mitral valve. The fixing completed by the suture locker 2000b specifically refers to the following. The distal end of the suture 3000 is enabled to extend out of an incision of the heart and penetrate into another suture lock pin 21000 of the suture locker 2000b. The mandrel 25000 and the collet push rod 26200 are pushed toward the distal end until the mandrel 25000 and the collet push rod 26200 approach the outer surface of the heart. The suture 3000 is then locked, and an unwanted portion of the suture 3000 is snipped. At this point, one lock pin 21000 stays in the heart, and below the two leaflets form the "double-orifice structure". The other lock pin 21000 is left on the outer surface of the heart to fix the distal end of the suture 3000. The fixing can also be done with traditional pledget or patches.

It will be appreciated that the adjustable heart valve repair system according to other implementations of the present disclosure can also be used to alleviate or treat the "tricuspid regurgitation", i.e., with the suture implanting apparatus, one or more sutures are implanted into multiple leaflets of the tricuspid valve, and the sutures in the two or three leaflets are fixed together by the suture locker, thereby alleviating or avoiding the "tricuspid regurgitation". The principle and structure of the adjustable heart valve repair system for the "tricuspid regurgitation" are substantially the same as those of the adjustable heart valve repair system for the "mitral regurgitation" in the implementation of the present disclosure, and details are not be described herein. It will be appreciated that the adjustable heart valve repair system according to the other implementations of the present disclosure can be applied to other minimally invasive surgical procedures, where for these procedures, sutures need to be implanted into several sheet-like tissues and then the sutures need to be fixed together.

The implementations of the present disclosure are described in detail above, and specific examples are used to explain the principles and implementations of the present disclosure. The illustration of the above implementations is only used to help in understanding the method and the core idea of the present disclosure. Also, according to the ideas of the present disclosure, those of ordinary skill in the art can make changes for specific implementations and application scopes. In summary, the content of this specification should not be construed as limiting the present disclosure.

What is claimed is:
1. An adjustable heart valve repair system comprising:
 a suture implanting apparatus operable to implant a suture into at least one leaflet of a heart valve; and
 a suture locker operable to fix the suture and comprising:
  a lock pin operable to receive or fix the suture;
  an outer shaft defining a receiving cavity, wherein the lock pin is disposed at a distal end of the receiving cavity;
  a handle comprising a fixing portion, wherein the fixing portion is coupled to a proximal end of the outer shaft; and
  an adjusting device disposed on the fixing portion, wherein the adjusting device is coupled to a proximal end of the suture and operable to adjust tensioning or loosening of the suture; wherein
 the suture implanting apparatus comprises:
  a pushing shaft;
  a clamping assembly operable to clamp the at least one leaflet, wherein the clamping assembly comprises a clamping push rod for receiving the suture, a distal clamp, and a proximal clamp, wherein the distal clamp and the proximal clamp are able to open and close relatively, the distal clamp is disposed at a proximal end of the clamping push rod, and the proximal clamp is disposed at a distal end of the pushing shaft;

a puncturing assembly operable to puncture the at least one leaflet; and a clamping auxiliary assembly comprising at least one clamping auxiliary arm movably received in the pushing shaft and at least one clamping auxiliary member each disposed at a distal end of one of the at least one clamping auxiliary arm, wherein the at least one clamping auxiliary member is made of an elastic and/or flexible material, and the at least one clamping auxiliary arm is operable to push the at least one clamping auxiliary member out of the distal end of the pushing shaft or a sidewall of the proximal clamp.

2. The adjustable heart valve repair system of claim 1, wherein the adjusting device comprises a bunching device, wherein the bunching device is movably coupled to the fixing portion and is coupled to the proximal end of the suture to adjust the tensioning or loosening of the suture.

3. The adjustable heart valve repair system of claim 2, wherein the adjusting device further comprises an adjusting rail, wherein the adjusting rail is disposed on the fixing portion, the bunching device is coupled to the fixing portion via the adjusting rail, and the bunching device is able to move backward and forward on the adjusting rail along an axial direction of the adjusting rail to adjust the tensioning or loosening of the suture.

4. The adjustable heart valve repair system of claim 3, wherein the bunching device comprises a suture fixation and a handle connecting portion coupled to the suture fixation, wherein the suture fixation is detachably coupled with the suture, the handle connecting portion is disposed in the adjusting rail, and the bunching device moves backward and forward on the adjusting rail along the axial direction of the adjusting rail via the handle connecting portion.

5. The adjustable heart valve repair system of claim 4, wherein the suture fixation comprises a spool, a first blocking portion, a second blocking portion, and an elastic sheet, wherein the first blocking portion and the second blocking portion are coupled to two ends of the spool, respectively, the second blocking portion is further away from the handle connecting portion than the first blocking portion, and the elastic sheet is fixed to the second blocking portion and operable to fix the suture.

6. The adjustable heart valve repair system of claim 4, wherein
the adjusting rail comprises a rail cavity and a rail outer wall; and
the handle connecting portion comprises an inserting end and a connecting shaft, wherein the inserting end is disposed in the rail cavity and able to move backward and forward in the rail cavity, the connecting shaft is disposed on the rail outer wall and able to move backward and forward on the rail outer wall, and the inserting end is coupled to the suture fixation via the connecting shaft.

7. The adjustable heart valve repair system of claim 6, wherein the rail outer wall is provided with first teeth, and the connecting shaft is provided with second teeth, wherein the first teeth are able to be engaged with the second teeth to enable the connecting shaft to roll on the rail outer wall.

8. The adjustable heart valve repair system of claim 4, wherein the adjusting device further comprises a lead screw, a bolt, and an adjusting knob, wherein the lead screw is fixed in the fixing portion along the axial direction of the adjusting rail, the bolt is fixed in the fixing portion, the lead screw passes through the bolt and is engaged with the bolt, a proximal end of the lead screw passes through a proximal end of the fixing portion and is coupled to the adjusting knob, the handle connecting portion is fixed to the lead screw, and the adjusting knob is able to adjust an axially forward or backward movement of the lead screw.

9. The adjustable heart valve repair system of claim 1, wherein
the handle further comprises a movable portion, wherein the movable portion is able to move with respect to the fixing portion;
the lock pin defines a hollow inner cavity along an axial direction of the lock pin, wherein the hollow inner cavity is configured to receive the suture and allow the suture to pass through; and
the suture locker further comprises:
a squeezing assembly operable to hold and press the lock pin to deform the lock pin;
a mandrel having a distal end coupled to a proximal end of the squeezing assembly and a proximal end movably coupled to the movable portion; and
the squeezing assembly and the mandrel are both received in the receiving cavity, the movable portion is able to move with respect to the fixing portion to drive the mandrel to move, so as to enable the squeezing assembly to hold and press the lock pin.

10. The adjustable heart valve repair system of claim 9, wherein the squeezing assembly comprises a squeezing collet and a collet push rod, wherein the squeezing collet comprises an upper clip, a lower clip, and a clip connecting portion disposed between a proximal end of the upper clip and a proximal end of the lower clip, wherein the lock pin is disposed between the upper clip and the lower clip, a proximal end of the collet push rod is coupled to the distal end of the mandrel, a distal end of the collet push rod is adjacent to the upper clip, and the mandrel drives the collet push rod to move toward the upper clip to push the upper clip toward the lower clip, so as to enable the upper clip and the lower clip to cooperatively hold and press the lock pin.

11. The adjustable heart valve repair system of claim 10, wherein the upper clip has a first surface facing the lock pin, and the lower clip has a second surface facing the lock pin, wherein the first surface is provided with a first engaging portion, and the second surface is provided with a second engaging portion, wherein the first engaging portion and the second engaging portion are able to be engaged with each other to enable the upper clip and the lower clip to be in a closed state.

12. The adjustable heart valve repair system of claim 10, wherein
the distal end of the collet push rod has a first inclined surface inclined downwardly from the distal end of the collet push rod to the proximal end of the collet push rod; and
the upper clip has a second inclined surface facing away from the lock pin, wherein the second inclined surface is inclined downwardly from the distal end of the upper clip to the proximal end of the upper clip, and the first inclined surface has a smaller slope than the second inclined surface.

13. The adjustable heart valve repair system of claim 9, wherein the outer shaft defines a suture inlet at a distal end of the outer shaft along a radial direction of the outer shaft and a suture outlet, wherein the suture inlet has a diameter at least equaling a diameter of a portion of the lock pin, wherein the portion of the lock pin has a maximum outer diameter, wherein the suture inlet and suture outlet both communicate with the hollow inner cavity of the lock pin.

14. The adjustable heart valve repair system of claim 13, wherein the outer shaft is provided with a holding portion at the distal end of the outer shaft, wherein the holding portion has a diameter gradually decreasing from a proximal end of the holding portion to a distal end of the holding portion, the holding portion has a holding portion end surface at the distal end of the holding portion, and the holding portion defines a holding portion opening along an axial direction of the holding portion, wherein the holding portion opening extends through the holding portion end surface and communicates with the receiving cavity.

15. The adjustable heart valve repair system of claim 14, wherein the holding portion opening comprises a protrusion protruding along a radial direction of the holding portion opening, wherein the protrusion and the holding portion end surface define a preset distance, and the lock pin is partially disposed in the holding portion opening to enable the protrusion to fix the lock pin.

16. The adjustable heart valve repair system of claim 15, wherein the lock pin is provided with a circular cone at a distal end of the lock pin, wherein the circular cone has a larger diameter than the proximal end of the lock pin, the circular cone is disposed in the holding portion opening, and the protrusion fixes the lock pin.

17. The adjustable heart valve repair system of claim 1, wherein each of the at least one clamping auxiliary member has a deformable structure and comprises an elastic member, wherein the elastic member is able to be switched between a compressed state and a stretched state, wherein an area of the elastic member in the stretched state is larger than that of the elastic member in the compressed state.

18. The adjustable heart valve repair system of claim 1, wherein
the suture implanting apparatus further comprises a detecting assembly, wherein the detecting assembly comprises at least one probe, wherein the at least one probe is movably received in the pushing shaft;
the proximal clamp defines at least one probe outlet corresponding to the at least one probe; the distal clamp defines at least one probe receiving cavity corresponding to the at least one probe; and
a distal end of each of the at least one probe extends out of one of the at least one probe outlet and is received in one of the at least one probe receiving cavity.

19. The adjustable heart valve repair system of claim 18, wherein each of the at least one probe comprises a probe body and a probe end disposed at a distal end of the probe body, wherein the probe body has a solid or hollow structure, and the probe end has a solid or hollow structure with a smooth outer surface.

20. An adjustable heart valve repair system comprising:
a suture implanting apparatus operable to implant a suture into at least one leaflet of a heart valve; and
a suture locker operable to fix the suture and comprising:
a lock pin operable to receive or fix the suture, wherein the lock pin defines a hollow inner cavity along an axial direction of the lock pin, and the hollow inner cavity is configured to receive the suture and allow the suture to pass through;
an outer shaft defining a receiving cavity, wherein the lock pin is disposed at a distal end of the receiving cavity;
a handle comprising a fixing portion and a movable portion, wherein the fixing portion is coupled to a proximal end of the outer shaft, and the movable portion is able to move with respect to the fixing portion;
an adjusting device disposed on the fixing portion, wherein the adjusting device is coupled to a proximal end of the suture and operable to adjust tensioning or loosening of the suture;
a squeezing assembly operable to hold and press the lock pin to deform the lock pin; and
a mandrel having a distal end coupled to a proximal end of the squeezing assembly and a proximal end movably coupled to the movable portion;
wherein the squeezing assembly and the mandrel are both received in the receiving cavity, and the movable portion is able to move with respect to the fixing portion to drive the mandrel to move, so as to enable the squeezing assembly to hold and press the lock pin,
wherein the squeezing assembly comprises a squeezing collet and a collet push rod,
wherein the squeezing collet comprises an upper clip, a lower clip, and a clip connecting portion disposed between a proximal end of the upper clip and a proximal end of the lower clip, and
wherein the lock pin is disposed between the upper clip and the lower clip, a proximal end of the collet push rod is coupled to the distal end of the mandrel, a distal end of the collet push rod is adjacent to the upper clip, and the mandrel drives the collet push rod to move toward the upper clip to push the upper clip toward the lower clip, so as to enable the upper clip and the lower clip to cooperatively hold and press the lock pin.

* * * * *